(12) United States Patent
Gao et al.

(10) Patent No.: US 11,479,785 B2
(45) Date of Patent: Oct. 25, 2022

(54) PLANTS HAVING ALTERED AGRONOMIC CHARACTERISTICS UNDER NITROGEN LIMITING CONDITIONS AND RELATED CONSTRUCTS AND METHODS INVOLVING ABIOTIC STRESS TOLERANCE GENES

(71) Applicants: SINOBIOWAY BIO-AGRICULTURE GROUP CO. LTD., Beijing (CN); PIONEER OVERSEAS CORPORATION, Johnston, IA (US)

(72) Inventors: Yang Gao, Beijing (CN); Guihua Lu, San Diego, CA (US); Guanfan Mao, Beijing (CN); Changgui Wang, Beijing (CN); Guokui Wang, Beijing (CN); Jiantao Wang, Beijing (CN)

(73) Assignees: SINOBIOWAY BIO-AGRICULTURE GROUP CO LTD; PIONEER OVERSEAS CORPORATION

( * ) Notice: Subject to any disclaimer, the term of this patent is extended or adjusted under 35 U.S.C. 154(b) by 0 days.

(21) Appl. No.: 17/045,989

(22) PCT Filed: Apr. 26, 2019

(86) PCT No.: PCT/CN2019/084462
§ 371 (c)(1),
(2) Date: Oct. 7, 2020

(87) PCT Pub. No.: WO2019/206256
PCT Pub. Date: Oct. 31, 2019

(65) Prior Publication Data
US 2021/0040496 A1    Feb. 11, 2021

(30) Foreign Application Priority Data
Apr. 28, 2018    (CN) .......................... 201810401144.6

(51) Int. Cl.
*C12N 15/82*    (2006.01)
*C07K 14/415*    (2006.01)

(52) U.S. Cl.
CPC ........ *C12N 15/8271* (2013.01); *C07K 14/415* (2013.01); *C12N 15/8213* (2013.01)

(58) Field of Classification Search
None
See application file for complete search history.

(56) References Cited

U.S. PATENT DOCUMENTS 7,214,786 B2    5/2007    Kovalic et al.

FOREIGN PATENT DOCUMENTS

WO    2012170304 A2    12/2012

OTHER PUBLICATIONS

Olsen et al. (2005) Trends Plant Sci 10(2):79-87.*
Hill & Preiss (1998) Biochem Biophys Res Commun 244(2):573-77.*
Zhang (2003) Curr Opin Plant Biol 6:430-40.*
Chen et al. (2006) Plant J 4873-84.*
Guo et al. (2004) Proc Natl Acad Sci USA 101:9205-10.*
Davies (2003) Nutr Rev 61 (s6):S124-34.*
Kawahara et al. (2013) Rice (6):4.*
GenBank Accession No. BAD87504.1, GenBank Database Feb. 16, 2008(Feb. 16, 2008).
GenBank Accession No. XP_015629507.1, GenBank Database Mar. 1, 2016 (Mar. 1, 2016).
GenBank Accession No. XP_015650713.1, GenBank Database Mar. 1, 2016 (Mar. 1, 2016).
GenBank Accession No. XP_015651155.1, GenBank Database Mar. 1, 2016 (Mar. 1, 2016).
International Search Report and Written Opnion for International Application PCT/CN2019/084462, dated Jul. 25, 2019.

* cited by examiner

*Primary Examiner* — Russell T Boggs

(57) ABSTRACT

Isolated polynucleotides and polypeptides, and recombinant DNA constructs useful for conferring improved nitrogen use efficiency; compositions (such as plants or seeds) comprising these recombinant DNA constructs; and methods utilizing these recombinant DNA constructs are disclosed. The recombinant DNA constructs comprise a polynucleotide operably linked to a promoter that is functional in a plant, wherein said polynucleotides encode abiotic stress tolerance polypeptides.

9 Claims, No Drawings

Specification includes a Sequence Listing.

PLANTS HAVING ALTERED AGRONOMIC CHARACTERISTICS UNDER NITROGEN LIMITING CONDITIONS AND RELATED CONSTRUCTS AND METHODS INVOLVING ABIOTIC STRESS TOLERANCE GENES

REFERENCE TO SEQUENCE LISTING SUBMITTED ELECTRONICALLY

The official copy of the sequence listing is submitted electronically via EFS-Web as an ASCII formatted sequence listing with a file named RTS22593J-US-PCT_SequenceListing_ST25.txt created on 22 Sep. 2020 and having a size of 27.8 kilobytes and is filed concurrently with the specification. The sequence listing comprised in this ASCII formatted document is part of the specification and is herein incorporated by reference in its entirety.

FIELD

The field of the disclosure relates to plant breeding and genetics and, particularly, relates to recombinant DNA constructs useful in plants for conferring nitrogen use efficiency and/or tolerance to nitrogen limiting conditions.

BACKGROUND

Stresses to plants may be caused by both biotic and abiotic agents. For example, biotic causes of stress include infection with pathogen, insect feeding, and parasitism by another plant such as mistletoe. Abiotic stresses include, for example, excessive or insufficient available water, deficiency of nutrient elements adversely, temperature extremes, and synthetic chemicals such as herbicides.

Abiotic stress is the primary cause of crop loss worldwide, causing average yield losses more than 50% for major crops (Boyer, J. S. (1982) Science 218:443-448; Bray, E. A. et al. (2000) In Biochemistry and Molecular Biology of Plants, edited by Buchannan, B. B. et al., Amer. Soc. Plant Biol., pp. 1158-1249). Plants are sessile and must adjust to the prevailing environmental conditions of their surroundings. This has led to their development of a great plasticity in gene regulation, morphogenesis, and metabolism. Adaptation and defense strategies involve the activation of genes encoding proteins important in the acclimation or defense towards the different stressors.

The absorption of nitrogen by plants plays an important role in their growth (Gallais et al., J. Exp. Bot. 55(396): 295-306 (2004)). Plants synthesize amino acids from inorganic nitrogen in the environment. Consequently, nitrogen fertilization has been a powerful tool for increasing the yield of cultivated plants, such as rice, maize and soybean. Lack of sufficient plant-available nitrogen for optimum growth and development may be considered as an abiotic stress. To avoid pollution by nitrates and maintain a sufficient profit margin, there is a need to reduce the use of nitrogen fertilizer.

Accordingly, there is a need to develop new compositions and method to improve nitrogen use efficiency. This invention provides such compositions and methods.

SUMMARY

The following embodiments are among those encompassed by the disclosure:

Provided is an isolated polynucleotide comprising: (a) a polynucleotide with nucleotide sequence of at least 85% identity to SEQ ID NO:1, 4, 7, 10 or 13; (b) a polynucleotide with a nucleotide sequence of at least 85% identity to SEQ ID NO: 2, 5, 8, 11 or 14; (c) a polynucleotide encoding a polypeptide comprising an amino acid sequence of at least 90% identity to SEQ ID NO: 3, 6, 9, 12 or 15; or (d) the full complement of the nucleotide sequence of (a), (b) or (c), wherein an increased expression of the polynucleotide in a plant increases nitrogen stress tolerance or improves NUE compared to a control not having the increased expression of the polynucleotide. In certain embodiments, the nucleotide sequence comprises SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 13 or SEQ ID NO: 14. In certain embodiments, the amino acid sequence of the polypeptide comprises SEQ ID NO: 3, SEQ ID NO: 6, SEQ ID NO: 9, SEQ ID NO: 12 or SEQ ID NO: 15

The present disclosure also provides a recombinant DNA construct comprising an isolated polynucleotide operably linked to at least one regulatory sequence, wherein the polynucleotide comprises: (a) a polynucleotide with a nucleotide sequence of at least 85% identity to SEQ ID NO: 1, 2, 4, 5, 7, 8, 10, 11, 13 or 14; (b) a polynucleotide encoding a polypeptide comprising an amino acid sequence of at least 90% identity to SEQ ID NO: 3, 6, 9, 12 or 15; or (c) the full complement of the nucleotide sequence of (a) or (b). In certain embodiments, the at least one regulatory sequence is a promoter functional in a plant.

Also provided is a modified plant or seed comprising an increased expression of at least one polynucleotide encoding a DN-LTP8, CYP76M5, FBX25, GH17, DN-LTP9 polypeptide compared to a control plant or seed, wherein the polynucleotide comprises: (a) a polynucleotide with a nucleotide sequence of at least 85% identity to SEQ ID NO: 1, 2, 4, 5, 7, 8, 10, 11, 13 or 14; (b) a polynucleotide encoding a polypeptide comprising an amino acid sequence of at least 90% identity to SEQ ID NO: 3, 6, 9, 12 or 15; wherein said plant exhibits improved nitrogen stress tolerance and/or enhanced yield when compared to the control plant.

In certain embodiments, the modified plant or seed comprises in its genome a recombinant DNA construct comprising a polynucleotide operably linked to at least one regulatory element, wherein the polynucleotide comprises: (a) a polynucleotide with a nucleotide sequence of at least 85% identity to SEQ ID NO: 1, 2, 4, 5, 7, 8, 10, 11, 13 or 14; (b) a polynucleotide encoding a polypeptide comprising an amino acid sequence of at least 90% identity to SEQ ID NO: 3, 6, 9, 12 or 15; or (c) the full complement of the nucleotide sequence of (a) or (b); wherein said plant exhibits improved nitrogen use efficiency (NUE) when compared to the control plant.

Also provided are methods of increasing nitrogen stress tolerance or NUE in a plant, comprising increasing the expression of at least one polynucleotide encoding a DN-LTP8, CYP76M5, FBX25, GH17, DN-LTP9 polypeptide in the plant compared to a control plant, wherein the polynucleotide comprises: (a) a polynucleotide with a nucleotide sequence of at least 85% identity to SEQ ID NO: 1, 4, 7, 10 or 13; (b) a polynucleotide with a nucleotide sequence of at least 85% identity to SEQ ID NO: 2, 5, 8, 11 or 14; (c) a polynucleotide encoding a polypeptide comprising an amino acid sequence of at least 90% identity to SEQ ID NO: 3, 6, 9, 12 or 15.

In certain embodiments, the expression of the polynucleotide is increased by: (a) increasing the expression of the polynucleotide encoding a DN-LTP8, CYP76M5, FBX25, GH17, DN-LTP9 polypeptide in plant by introducing a recombinant DNA construct into the plant, wherein the recombinant DNA construct comprises the polynucleotide encoding the DN-LTP8, CYP76M5, FBX25, GH17, DN-LTP9 polypeptide operably linked to at least one heterologous regulatory element, wherein the polynucleotide encodes the polypeptide comprising an amino acid sequence of at least 90% identity compared to SEQ ID NO: 3, 6, 9, 12 or 15; or (b) introducing a genetic modification that increases the expression and/or activity of an endogenous polynucleotide encoding the polypeptide having an amino acid sequence of at least 90% identity compared to SEQ ID NO: 3, 6, 9, 12 or 15.

SEQUENCE IDENTIFICATION

The disclosure can be more fully understood from the following detailed description and Sequence Listing which form a part of this application.

TABLE 1

Nucleotide and Amino Acid Sequences Provided in the Sequence Listing

| Source species | Clone Designation | SEQ ID NO: (Nucleotide) | SEQ ID NO: (Amino Acid) |
|---|---|---|---|
| Oryza sativa | OsDN-LTP8 | 1, 2 | 3 |
| Oryza sativa | OsCYP76M5 | 4, 5 | 6 |
| Oryza sativa | OsFBX25 | 7, 8 | 9 |
| Oryza sativa | OsGH17 | 10, 11 | 12 |
| Oryza sativa | OsDN-LTP9 | 13, 14 | 15 |
| Artificial | Primers | 16-33 | n/a |

The Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The term "OsDN-LTP8 (Low nitrogen Tolerance Protein 8)" refers to a rice polypeptide that confers a low nitrogen tolerance phenotype and is encoded by the rice gene locus LOC_Os09g26530.1 and any associated allelic variants thereof. "DN-LTP8 polypeptide" refers herein to the OsDN-LTP8 polypeptide and its homologs from other organisms.

The OsDN-LTP8 polypeptide (SEQ ID NO: 3) is encoded by the coding sequence (CDS) (SEQ ID NO: 2) or nucleotide sequence (SEQ ID NO: 1) at rice gene locus LOC_Os09g26530.1. This polypeptide is annotated as "expressed protein" in TIGR (rice.plantbiology.msu.edu/index.shtml), and "uncharacterized protein" in NCBI (ncbi.nlm.nih.gov/).

The term "OsCYP76M5 (cytochrome P450 76M5)" refers to a rice polypeptide that confers a low nitrogen tolerance phenotype and is encoded by the rice gene locus LOC_Os08g43440.1 and any associated allelic variants thereof. "CYP76M5 polypeptide" refers herein to the OsCYP76M5 polypeptide and its homologs from other organisms.

The OsCYP76M5 polypeptide (SEQ ID NO: 6) is encoded by the coding sequence (CDS) (SEQ ID NO: 5) or nucleotide sequence (SEQ ID NO: 4) at rice gene locus LOC_Os08g43440.1. This polypeptide is annotated as "cytochrome P450, putative, expressed" in TIGR and "cytochrome P450 76M5-like" in NCBI.

The term "OsFBX25" refers to a rice polypeptide that confers a low nitrogen tolerance phenotype and is encoded by the rice gene locus LOC_Os01g55210.1 and any associated allelic variants thereof. "FBX25 polypeptide" refers herein to the OsFBX25 polypeptide and its homologs from other organisms.

The OsFBX25 polypeptide (SEQ ID NO: 9) is encoded by the coding sequence (CDS) (SEQ ID NO: 8) or nucleotide sequence (SEQ ID NO: 7) at rice gene locus LOC_Os01g55210.1. This polypeptide is annotated as "OsFBX25-F-box domain containing protein, expressed" in TIGR and "hypothetical protein" in NCBI.

The term "OsGH17 (glycosyl hydrolases family 17)" refers to a rice polypeptide that confers a low nitrogen tolerance phenotype and is encoded by the rice gene locus LOC_Os03g22530.1 and any associated allelic variants thereof. "GH17 polypeptide" refers herein to the OsGH17 polypeptide and its homologs from other organisms.

The OsGH17 polypeptide (SEQ ID NO: 12) is encoded by the coding sequence (CDS) (SEQ ID NO: 11) or nucleotide sequence (SEQ ID NO: 10) at rice gene locus LOC_Os03g22530.1. This polypeptide is annotated as "glycosyl hydrolases family 17, putative, expressed" in TIGR and "lichenase-2-like" in NCBI.

The term "OsDN-LTP9 (Low nitrogen Tolerance Protein 9)" refers to a rice polypeptide that confers a low nitrogen tolerance phenotype and is encoded by the rice gene locus LOC_Os04g57804.1 and any associated allelic variants thereof. "DN-LTP9 polypeptide" refers herein to the OsDN-LTP9 polypeptide and its homologs from other organisms.

The OsDN-LTP9 polypeptide (SEQ ID NO: 15) is encoded by the coding sequence (CDS) (SEQ ID NO: 14) or nucleotide sequence (SEQ ID NO: 13) at rice gene locus LOC_Os04g57804.1. This polypeptide is annotated as "expressed protein" in TIGR.

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Modified plant" includes reference to a plant which comprises within its genome a heterologous polynucleotide or modified gene or promoter. For example, the heterologous polynucleotide is stably integrated within the genome such that the polynucleotide is passed on to successive generations. The heterologous polynucleotide may be integrated into the genome alone or as part of a recombinant DNA construct. A T0 plant is directly recovered from the transformation and regeneration process. Progeny of T0 plants are referred to as T1 (first progeny generation), T2 (second progeny generation), etc.

"Heterologous" with respect to sequence means a sequence that originates from a foreign species, or, if from the same species, is substantially modified from its native form in composition and/or genomic locus by deliberate human intervention.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control" or "control plant" or "control plant cell" provides a reference point for measuring changes in phenotype of a subject plant or plant cell which was genetically altered by, such as transformation, and has been affected as to a gene of interest. A subject plant or plant cell may be descended from a plant or cell so altered and will comprise the alteration. Typically, the control plant is a wild-type plant or cell, i.e., of the same genotype as the starting material for the genetic alteration which resulted in the subject plant or cell.

The term "trait" refers to a physiological, morphological, biochemical, or physical characteristics of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar or nitrogen concentrations, or by the observation of the expression level of a gene or genes, or by agricultural observations such as osmotic stress tolerance or yield.

"Agronomic characteristics" is a measurable parameter including but not limited to, greenness, yield, growth rate, biomass, fresh weight, dry weight at maturation, fruit yield, seed yield, total plant nitrogen content, fruit nitrogen content, seed nitrogen content, nitrogen content in vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, and ear length, early seedling vigor, and seedling emergence under low temperature stress.

Increased biomass can be measured, for example, as an increase in plant height, plant total leaf area, plant fresh weight, plant dry weight or plant grain yield, as compared with control plants.

The ability to increase the biomass or size of a plant would have several important commercial applications. Crop cultivars may be developed to produce higher yield of the vegetative portion of the plant, to be used in food, feed, fiber, and/or biofuel.

Increased leaf size may be of particular interest. Increased leaf biomass can be used to increase production of plant-derived pharmaceutical or industrial products.

Increased tiller number may be of particular interest and can be used to increase yield. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including nutrient deprivation and/or water deprivation, because larger roots may better reach or take up nutrients and/or water.

"Nitrogen limiting conditions" refers to conditions where the amount of total available nitrogen (e.g., from nitrates, ammonia, or other known sources of nitrogen) is not sufficient to sustain optimal plant growth and development. One skilled in the art would recognize conditions where total available nitrogen is sufficient to sustain optimal plant growth and development. One skilled in the art would recognize what constitutes sufficient amounts of total available nitrogen, and what constitutes soils, media and fertilizer inputs for providing nitrogen to plants. Nitrogen limiting conditions will vary depending upon a number of factors, including but not limited to, the particular plant and environmental conditions.

"Increased nitrogen stress tolerance" of a plant is measured relative to a reference or control plant, reflects ability of the plant to survive and/or grow better under nitrogen limiting conditions, and means that the nitrogen stress tolerance of the plant is increased by any amount when compared to the nitrogen stress tolerance of the reference or control plant. For example, a plant with "increased nitrogen stress tolerance" may have a higher grain yield when grown under low nitrogen conditions compared to a control plant grown under the same conditions.

"NUE" is nitrogen utilization efficiency and refers to a plant's ability to utilize nitrogen in low or high levels of fertilizer. It reflects the plant's ability to uptake, assimilate, and/or otherwise utilize nitrogen.

Soil plant analyses development (SPAD) value is SPAD reading which is measured by SPAD-502 plus (a chlorophyll meter, made by KONICA MINOLTA). The SPAD value is relative content of leaf chlorophyll and an important indicator of plant health. Many studies indicated that a significant and positive correlation was observed between leaf nitrogen content and SPAD value (Swain D. K. and Sandip S. J. (2010) *Journal of Agronomy* 9 (2):38-44), and leaf SPAD value is used as index of nitrogen status diagnosis in crops (Cai H.-G. et al. (2010) *Acta metallurgica sinica* 16 (4): 866-873).

"Chlorate" refers to a chemical compound containing chlorate anion, a salt of chloric acid. It is a nitrate analog which can be uptake by plant with same transport system like nitrate, and then converted by nitrate reductase to chlorite which is toxic and leads to plant damage, withering, and plant death. Potassium chlorate is used in this disclosure.

"Chlorate sensitivity" is a trait of plant, reflects the level of damage, even death after chlorate uptake, transport or reduction when treated with chlorate solution, compared to a reference or control plant. In general, chlorate sensitivity can be used as a marker of NUE. The more sensitive plants are to chlorate, the higher the NUE.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenine or deoxyadenine (for RNA or DNA, respectively), "C" for cytosine or deoxycytosine, "G" for guanine or deoxyguanine, "U" for uracil, "T" for thymine or deoxythymine, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source but arranged in a manner different than that normally found in nature.

"Regulatory sequences" and "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably and refer to a promoter that is expressed predominantly but not necessarily exclusively in one tissue or organ, but that may also be expressed in one specific cell or cell type.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hem izygous at that locus.

A "gene" refers to a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. A mutated plant is a plant comprising a mutated gene.

As "targeted mutation" is a mutation in a native gene that was made by altering a target sequence within the native gene using a method involving a double-strand-break-inducing agent that is capable of inducing a double-strand break in the DNA of the target sequence as disclosed herein of known in the art.

"Genetic modification" refers to a change or alteration in the genomic nucleic acid sequence of a plant introduced by deliberate human activity.

"CRISPR-associated genes" refers to nucleic acid sequences that encode polypeptide components of clustered regularly interspersed short palindromic repeats (CRISPR)-associated systems (Cas), and the genes are generally coupled, associated or close to or in the vicinity of flanking CRISPR loci. The terms "Cas gene", "CRISPR-associated gene" are used interchangeably herein. Examples include, but are not limited to, Cas3 and Cas9, which encode endonucleases from the CRISPR type I and type II systems, respectively.

"Cas endonuclease" refers to a Cas protein encoded by a Cas gene, wherein said Cas protein is capable of introducing a double strand break into a DNA target sequence. The Cas endonuclease is guided by the guide polynucleotide to recognize and optionally introduce a double strand break at a specific target site into the genome of a cell.

"Guide RNA (gRNA)" refers to a crRNA (CRISPR RNA): tracrRNA fused hybrid RNA molecule encoded by a customizable DNA element that, generally, comprises a copy of a spacer sequence which is complementary to the protospacer sequence of the genomic target site, and a binding domain for an associated-Cas endonuclease of the CRISPR complex.

"Guide polynucleotide" refers to a polynucleotide sequence that can form a complex with a Cas endonuclease and enables the Cas endonuclease to recognize and optionally cleave a DNA target site. The guide polynucleotide can be comprised of a single molecule or a double molecule.

The term "guide polynucleotide/Cas endonuclease system" refers to a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is approximately oriented at the 3' end of the target sequence.

"Genomic target site" refers to a protospacer and a protospacer adjacent motif (PAM) located in a host genome selected for targeted mutation and/or double-strand break.

"Protospacer" refers to a short DNA sequence (12 to 40 bp) that can be targeted for mutation, and/or double-strand break, mediated by enzymatic cleavage with a CRISPR system endonuclease guided by complementary base-pairing with the spacer sequence in the crRNA or sgRNA.

"Protospacer adjacent motif (PAM)" includes a 3 to 8 bp sequence immediately adjacent to the protospacer sequence in the genomic target site.

CRISPR loci (Clustered Regularly Interspaced Short Palindromic Repeats) (also known as SPIDRs-SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 bp by depending on the CRISPR locus (WO2007/025097 published Mar. 1, 2007).

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more (patent application WO-PCT PCT/US12/30061 filed on Mar. 22, 2012). Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates.

TAL effector nucleases are a new class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, FokI. The unique, modular TAL effector DNA binding domain allows for the design of proteins with potentially any given DNA recognition specificity (Miller et al. (2011) Nature Biotechnology 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs consist of an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

The terms "target site", "target sequence", "target DNA", "target locus", "genomic target site", "genomic target sequence", and "genomic target locus" are used interchangeably herein and refer to a polynucleotide sequence in the genome (including choloroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature. As used herein, terms "endogenous target sequence" and "native target sequence" are used interchangeable herein to refer to a target sequence that is endogenous or native to the genome of a plant and is at the endogenous or native position of that target sequence in the genome of the plant.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

Turning now to the embodiments:

Embodiments include isolated polynucleotides and polypeptides, recombinant DNA constructs useful for conferring improved nitrogen use efficiency, compositions (such as plants or seeds) comprising these recombinant DNA constructs, and methods utilizing these recombinant DNA constructs.

Isolated Polynucleotides and Polypeptides

The present disclosure includes the following isolated polynucleotides and polypeptides:

An isolated polynucleotide comprising: (i) a nucleic acid sequence encoding a polypeptide comprising an amino acid sequence of at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12 or 15; or (ii) a full complement of the nucleic acid sequence of (i). In certain embodiments, increased expression of the polypeptide increases plant low nitrogen tolerance/NUE activity.

An isolated polypeptide having an amino acid sequence of at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12 or 15.

An isolated polynucleotide comprising (i) a nucleic acid sequence of at least 70% (e.g., 71%, 72%, 73%, 74%, 75%, 76%, 77%, 78%, 79%, 80%, 81%, 82%, 83%, 84%, 85%, 86%, 87%, 88%, 89%, 90%, 91% 92%, 93%, 94%, 95%, 96%, 97%, 98%, 99, or 100%) sequence identity to SEQ ID NO: 1, 2, 4, 5, 7, 8, 10, 11, 13 or 14; or (ii) a full complement of the nucleic acid sequence of (i). In certain embodiments, increased expression of the polynucleotide increases plant low nitrogen tolerance activity.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Recombinant DNA Constructs

In one aspect, the present disclosure includes recombinant DNA constructs.

In one embodiment, the recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12 or 15; or (ii) a full complement of the nucleic acid sequence of (i).

In another embodiment, the recombinant DNA construct comprises a polynucleotide operably linked to at least one regulatory sequence (e.g., a promoter functional in a plant), wherein said polynucleotide comprises (i) a nucleic acid sequence of at least 70% (e.g., 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 1, 2, 4, 5, 7, 8, 10, 11, 13 or 14; or (ii) a full complement of the nucleic acid sequence of (i).

In another embodiment, the recombinant DNA construct comprises a polynucleotide operably linked to at least one regulatory sequence (e.g., a promoter functional in a plant), wherein the said polynucleotide encodes a DN-LTP8, CYP76M5, FBX25, GH17 or DN-LTP9 protein.

Regulatory Sequences:

The recombinant DNA construct of the present disclosure may comprise at least one regulatory sequence.

In certain embodiments, the regulatory sequence may be a promoter or enhancer.

A number of promoters can be used in recombinant DNA constructs of the present disclosure. The promoters can be selected based on the desired outcome, and may include constitutive, tissue-specific, inducible, or other promoters for expression in the host organism.

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present disclosure which causes the desired temporal and spatial expression.

Promoters which are seed or embryo-specific and may be useful in the disclosure include soybean Kunitz trypsin inhibitor (Kti3, Jofuku and Goldberg, *Plant Cell* 1:1079-1093 (1989)), patatin (potato tubers) (Rocha-Sosa, M., et al., *EMBO J.* 8:23-29 (1989)), convicilin, vicilin, and legumin (pea cotyledons) (Rerie, W G., et al., *Mol. Gen. Genet.* 259:149-157 (1991); Newbigin, E. J., et al., *Planta* 180:461-470 (1990); Higgins, T. J. V., et al., *Plant. Mol. Biol.* 11:683-695 (1988)), zein (maize endosperm) (Schemthaner, J. P., et al., *EMBO J.* 7:1249-1255 (1988)), phaseolin (bean cotyledon) (Segupta-Gopalan, C., et al., *Proc. Natl. Acad. Sci. U.S.A.* 82:3320-3324 (1995)), phytohemagglutinin (bean cotyledon) (Voelker, T. et al., *EMBO J.* 6:3571-3577 (1987)), B-conglycinin and glycinin (soybean cotyledon) (Chen, Z-L, et al., *EMBO J.* 7:297-302 (1988)), glutelin (rice endosperm), hordein (barley endosperm) (Marris, C., et al., *Plant Mol. Biol.* 10:359-366 (1988)), glutenin and gliadin (wheat endosperm) (Colot, V., et al., *EMBO J.* 6:3559-3564 (1987)), and sporamin (sweet potato tuberous root) (Hattori, T., et al., *Plant Mol. Biol.* 14:595-604 (1990)). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J.* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current disclosure include the following: 1) the stress-inducible RD29A promoter (Kasuga et al., *Nature Biotechnol.* 17:287-91 (1999)); 2) the barley promoter, B22E; expression of B22E is specific to the pedicel in developing maize kernels ("Primary Structure of a Novel Barley Gene Differentially Expressed in Immature Aleurone Layers", Klemsdal et al., *Mol. Gen. Genet.* 228 (1/2):9-16 (1991)); and 3) maize promoter, Zag2 ("Identification and molecular characterization of ZAG1, the maize homolog of the *Arabidopsis* floral homeotic gene AGAMOUS", Schmidt et al., *Plant Cell* 5(7):729-737 (1993); "Structural characterization, chromosomal localization and phylogenetic evaluation of two pairs of AGAMOUS-like MADS-box genes from maize", Theissen et al., *Gene* 156 (2):155-166 (1995); NCBI GenBank Accession No. X80206)). Zag2 transcripts can be detected five days prior to pollination to seven to eight days after pollination ("DAP") and directs expression in the carpel of developing female inflorescences and Ciml which is specific to the nucleus of developing maize kernels. Ciml transcript is detected four to five days before pollination to six to eight DAP. Other useful promoters include any promoter which can be derived from a gene whose expression is maternally associated with developing female florets.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all its final mass, and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Cim1 that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp. (WO 00/12733), herein incorporated by reference. Additional early kernel/embryo promoters that find use in certain methods of the present disclosure include the seed-preferred promoter ltp2 (U.S. Pat. No. 5,525,716); maize Zm40 promoter (U.S. Pat. No. 6,403,862); maize nuc1c (U.S. Pat. No. 6,407,315); maize ckxl-2 promoter (U.S. Pat. No. 6,921,815 and US Patent Application Publication Number 2006/0037103); maize lec1 promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007).

Additional promoters for regulating the expression of the nucleotide sequences of the present disclosure in plants are stalk-specific promoters. Such stalk-specific promoters include the alfalfa S2A promoter (GenBank Accession No. EF030816; Abrahams et al., *Plant Mol. Biol.* 27:513-528 (1995)) and S2B promoter (GenBank Accession No. EF030817) and the like, herein incorporated by reference.

Promoters may be derived in their entirety from a native gene or be composed of different elements derived from different promoters found in nature, or even comprise synthetic DNA segments.

Additional examples of promoters for use in the compositions and methods described herein include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (GenBank Accession No. EF030817), and the constitutive promoter GOS2 from *Zea mays*. Other promoters include root preferred promoters, such as the maize NAS2 promoter, the maize Cyclo promoter (US Publication No. 2006/0156439, published Jul. 13, 2006), the maize ROOTMET2 promoter (WO 2005/063998, published Jul. 14, 2005), the CR1BIO promoter (WO 2006/055487, published May 26, 2006), the CRWAQ81 (WO 2005/035770, published Apr. 21, 2005) and the maize ZRP2.47 promoter (NCBI Accession No. U38790; NCBI GI No. 1063664).

Recombinant DNA constructs (and suppression DNA constructs) of the present disclosure may also include other regulatory sequences including, but not limited to, translation leader sequences, introns, and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)).

Compositions:

Provided is a plant comprising in its genome any of the recombinant DNA constructs described herein. Also provided are plants comprising a targeted genetic modification that increases the level and/or activity of a polynucleotide encoding any of the polypeptides described herein. In certain embodiments, the targeted genetic modification is the insertion of a heterologous promoter operably linked to a polynucleotide described herein.

Compositions also include any progeny of the plant, and any seed obtained from the plant or its progeny, wherein the progeny or seed comprises within its genome the recombinant DNA construct or targeted genetic modification. Progeny includes subsequent generations obtained by self-pollination or out-crossing of a plant. Progeny also includes hybrids and inbreds.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

Embodiments include but are not limited to the following:

1. A plant (for example, a rice, maize or soybean plant) comprising in its genome a recombinant DNA construct comprising a polynucleotide operably linked to at least one regulatory sequence, wherein said polynucleotide encodes a polypeptide having an amino acid sequence of at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12 or 15; and wherein said plant exhibits increased nitrogen stress tolerance when compared to a control plant not comprising said recombinant DNA construct. The plant may further exhibit an alteration of at least one agronomic characteristic when compared to the control plant.

2. A plant (for example, a rice, maize or soybean plant) comprising in its genome a targeted genetic modification at a genomic locus comprising a polypeptide having an amino acid sequence of at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12 or 15, and wherein the introduced genetic modification increases the expression and/or activity of the polypeptide and the said plant exhibits increased nitrogen stress tolerance when compared to a control plant.

3. Any progeny of the above plants in embodiment 1-2, any seeds of the above plants in embodiment 1-2, any seeds of progeny of the above plants in embodiment 1-2, and cells from any of the above plants in embodiment 1-2 and progeny thereof.

One of ordinary skill in the art is familiar with protocols for simulating nitrogen conditions, whether limiting or non-limiting, and for evaluating plants that have been subjected to simulated or naturally-occurring nitrogen conditions, whether limiting or non-limiting. For example, one can simulate nitrogen conditions by giving plants less nitrogen than normally required or no nitrogen over a period of time, and one can evaluate such plants by looking for differences in agronomic characteristics, e.g., changes in physiological and/or physical condition, including (but not limited to) vigor, growth, size, or root length, or in particular, leaf color or leaf area size. Other techniques for evaluating such plants include measuring chlorophyll fluorescence, photosynthetic rates, root growth or gas exchange rates.

In certain embodiments, nitrogen stress tolerance is evaluated by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring low or high nitrogen conditions (e.g., by measuring for substantially equivalent yield under low or high nitrogen conditions compared to normal nitrogen conditions, or by measuring for less yield loss under low or high nitrogen conditions compared to a control or reference plant).

SPAD value can be measured during low or high nitrogen condition in the field and greenhouse test by a chlorophyll meter. The SPAD value is a parameter indicating the plant health, and reflects plant nitrogen content by predicting the chlorophyll content. The plants with higher low nitrogen tolerance will have higher SPAD value compared to a control or reference plant.

Parameters such as gene expression level, level or activity of an encoded protein, SPAD value, tiller number, grain yield and others are typically presented with reference to a control cell or control plant. One of ordinary skill in the art would readily recognize a suitable control or reference plant to be utilized when assessing or measuring an agronomic characteristic or phenotype of a transgenic plant in any embodiment of the present disclosure in which a control is utilized (e.g., compositions or methods as described herein). For example, by way of non-limiting illustrations:

Methods:

Provided is a method of increasing nitrogen stress tolerance and/or chlorate sensitivity in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12 or 15; and (b) regenerating a transgenic plant from the regenerable plant cell after step (a), wherein the transgenic plant comprises in its genome the recombinant DNA construct and exhibits increased nitrogen stress tolerance and/or chlorate sensitivity when compared to a control plant not comprising the recombinant DNA construct. The method may further comprise (c) obtaining a progeny plant derived from the transgenic plant, wherein said progeny plant comprises in its genome the recombinant DNA construct and exhibits increased nitrogen stress tolerance and/or chlorate sensitivity when compared to a control plant not comprising the recombinant DNA construct.

Also provided is a method of increasing nitrogen stress tolerance and/or chlorate sensitivity in a plant, comprising: (a) introducing into a regenerable plant cell a targeted genetic modification at a genomic locus comprising a polynucleotide encoding a polypeptide having an amino acid sequence of at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12 or 15, wherein the targeted genetic modification increases the level and/or activity of the encoded polypeptide; and (b) regenerating a transgenic plant from the regenerable plant cell after step (a), wherein the transgenic plant comprises in its genome the targeted genetic modification and exhibits increased nitrogen stress tolerance and/or chlorate sensitivity when compared to a control plant not comprising the recombinant DNA construct. The method may further comprise (c) obtaining a progeny plant derived from the transgenic plant, wherein said progeny plant comprises in its genome the targeted genetic modification and exhibits increased nitrogen stress tolerance and/or chlorate sensitivity when compared to a control plant not comprising the targeted genetic modification.

Also provided is a method of evaluating nitrogen stress tolerance and/or chlorate sensitivity in a plant, comprising (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12 or 15; (b) regenerating a transgenic plant from the regenerable plant cell after step (a), wherein the transgenic plant comprises in its genome the recombinant DNA construct; and (c) evaluating the transgenic plant for nitrogen stress tolerance and/or chlorate sensitivity compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for nitrogen stress tolerance and/or chlorate sensitivity compared to a control plant not comprising the recombinant DNA construct.

Also provided is a method of determining an alteration of an agronomic characteristic in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12 or 15; (b) regenerating a transgenic plant from the regenerable plant cell after step (a), wherein the transgenic plant comprises in its genome said recombinant DNA construct; and (c) determining whether the transgenic plant exhibits an alteration of at least one agronomic characteristic when compared, optionally under nitrogen limiting conditions, to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration of at least one agronomic characteristic when compared, optionally under nitrogen limiting conditions, to a control plant not comprising the recombinant DNA construct.

In any of the preceding methods or any other embodiments of methods of the present disclosure, the step of determining an alteration of an agronomic characteristic in a transgenic plant, if applicable, may comprise determining whether the transgenic plant exhibits an alteration of at least one agronomic characteristic when compared, under varying environmental conditions, to a control plant not comprising the recombinant DNA construct.

In any of the preceding methods or any other embodiments of methods of the present disclosure, the step of determining an alteration of an agronomic characteristic in a progeny plant, if applicable, may comprise determining whether the progeny plant exhibits an alteration of at least one agronomic characteristic when compared, under varying environmental conditions, to a control plant not comprising the recombinant DNA construct.

In any of the preceding methods or any other embodiments of methods of the present disclosure, in said introducing step said regenerable plant cell may comprises a callus cell, an embryogenic callus cell, a gametic cell, a meristematic cell, or a cell of an immature embryo. The regenerable plant cells may derive from an inbred maize plant.

In any of the preceding methods or any other embodiments of methods of the present disclosure, said regenerating step may comprise: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present disclosure, the plant may exhibit the alteration of at least one agronomic characteristic when compared, under nitrogen stress conditions, to a control plant not comprising said recombinant DNA construct.

In any of the preceding methods or any other embodiments of methods of the present disclosure, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant disclosure.

The introduction of recombinant DNA constructs of the present disclosure into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

In addition, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" or engineered endonucleases such as meganucleases produced to modify plant genomes (see e.g., WO 2009/114321; Gao et al. (2010) Plant Journal 1:176-187). Another site-directed engineering is through the use of zinc finger domain recognition coupled with the restriction properties of restriction enzyme (See e.g., Urnov, et al., (2010) Nat Rev Genet. 11(9):636-46; Shukla, et al., (2009) Nature 459 (7245):437-41). A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The CRISPR/Cas system allows targeted cleavage of genomic DNA guided by a customizable small noncoding RNA.

Stacking of Traits in Transgenic Plant:

Transgenic plants may comprise a stack of one or more drought tolerance polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and cotransformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or over-expression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

EXAMPLES

The present disclosure is further illustrated in the following examples, in which parts and percentages are by weight and degrees are Celsius, unless otherwise stated. It should be understood that these examples, while indicating embodiments of the disclosure, are given by way of illustration only. From the above discussion and these examples, one skilled in the art can ascertain the essential characteristic of this disclosure, and without departing from the spirit and scope thereof, can make various changes and modifications of the disclosure to adapt it to various usages and conditions. Furthermore, various modifications of the disclosure in addition to those shown and described herein will be apparent to those skilled in the art from the foregoing description. Such modifications are also intended to fall within the scope of the appended claims.

Example 1

Cloning and Vector Construction of Abiotic Stress Tolerance Genes

Based on our preliminary screening of the rice activation tagging population and the sequence information of gene IDs shown in the Table 2, primers were designed for cloning rice genes of OsDN-LTP8, OsCYP76M5, OsFBX25, OsGH17 and OsDN-LTP9. The primers and the expected-lengths of the amplified genes are shown in Table 3.

For OsDN-LTP9, its cDNA was cloned by PCR using pooled cDNA from leaf, stem and root tissues of Zhonghua 11 plant as the template. For OsDN-LTP8, OsCYP76M5, OsFBX25 and OsGH17, their gDNAs were cloned, and amplified using genomic DNA of Zhonghua 11 as the template.

TABLE 2

Rice gene names, Gene IDs (from TIGR) and Construct IDs

| Gene name | Gene LOC ID | Construct ID |
|---|---|---|
| OsDN-LTP8 | LOC_Os09g26530 | DP0749 |
| OsCYP76M5 | LOC_Os08g43440 | DP0788 |
| OsFBX25 | LOC_Os01g55210 | DP0963 |
| OsGH17 | LOC_Os03g22530 | DP0979 |
| OsDN-LTP9 | LOC_Os04g57804 | DP1154 |

TABLE 3

Primers for cloning rice abiotic stress tolerance genes

| Primer | Sequence | SEQ ID NO: | Gene name | Length of amplified fragment (bp) |
|---|---|---|---|---|
| gc-1113 | 5'-CATTGGCTAATTTGTAAT TGG-3' | 16 | OsDN-LTP8 | 2128 |
| gc-1114 | 5'-CTATGGTGAACAATAGAA AACTGTG-3' | 17 | | |
| gc-4933 | 5'-GATTAGCTCCATTTTCCA CCTAAGAG-3' | 18 | OsCYP76M5 | 1728 |
| gc-4934 | 5'-CTACAATTATAGCCCGAG ATTTAAAACC-3' | 19 | | |
| gc-7143 | 5'-CTGCTGAGGCCCGTGTGC TACCTGTACCCATG-3' | 20 | OsGH17 | 636 |
| gc-7144 | 5'-CCGCTGAGGGGAGAGAG GAGCCAGCCGAGC-3' | 21 | | |
| gc-1176 | 5'-CCGTTCGGACAGTGAGG AGAAAGC-3' | 22 | OsFBX25 | 559 |
| gc-1177 | 5'-CCTCTCTTCTTCACGGG CTCCAGC-3' | 23 | | |
| gc-8676 | 5'-GGTCTCTCTTGCACTCG TGAGC-3' | 24 | OsDN-LTP9 | 278 |
| gc-8677 | 5'-CAAAATCAAGAACAGTA GCAGCCAG-3' | 25 | | |

The PCR amplified products were extracted after the agarose gel electrophoresis using a column kit and then ligated with TA cloning vectors. The sequences and orientation in these constructs were confirmed by sequencing. Then these genes were cloned into plant binary construct DP0158 (pCAMBIA1300-DsRed).

The generated expression vectors are listed in Table 2. The cloned nucleotide sequence in the construct of DP0749 and coding sequence of OsDN-LTP8 are provided as SEQ ID NO: 1 and 2, the encoded amino acid sequence of OsDN-LTP8 is SEQ ID NO: 3; the cloned nucleotide sequence in construct of DP0788 and coding sequence of OsCYP76M5 are provided as SEQ ID NO: 4 and 5, the encoded amino acid sequence of OsCYP76M5 is SEQ ID NO: 6; the cloned nucleotide sequence in construct of DP0963 and coding sequence of OsFBX25 are provided as SEQ ID NO: 7 and 8, the encoded amino acid sequence of OsFBX25 is SEQ ID NO: 9; the cloned nucleotide sequence in construct of DP0979 and coding sequence of OsGH17 are provided as SEQ ID NO: 10 and 11, the encoded amino acid sequence of OsGH17 is SEQ ID NO: 12; and the cloned nucleotide sequence in construct of DP1154 and coding sequence of OsDN-LTP9 are provided as SEQ ID NO: 13 and 14, the encoded amino acid sequence of OsDN-LTP9 is SEQ ID NO: 15

Example 2

Transformation to Obtain Transgenic Rice Lines

The vectors prepared in Example 1 or an empty vector (DP0158) were transformed into Zhonghua 11 (*Oryza sativa* L.) by the Agrobacteria-mediated method as described by Lin and Zhang ((2005) *Plant Cell Rep.* 23:540-547). Zhonghua 11 was cultivated by the institute of crop sciences, Chinese Academy of Agricultural Sciences. The first batch of seeds used in this research was provided by Beijing Weiming Kaituo Agriculture Biotech Co., Ltd. Calli induced from embryos were transformed with Agrobacteria with the vector. Transgenic seedlings (T0) generated in transformation laboratory were transplanted in the field to get T1 seeds. The T1 and T2 seeds were stored at cold room (4° C.). The expression vectors contain marker genes. T1 and T2 seeds which showed red color under green fluorescent light were transgenic seeds and were used in the following trait screening.

Example 3

Gene Expression Analysis

The gene expression levels in the transgenic rice plants were analyzed. A standard RT-PCR or a real-time RT-PCR procedure was used. EF-1α gene was used as an internal control to show that the amplification and loading of samples from the transgenic rice and the controls were similar. Gene expression was normalized based on the EF-1α mRNA levels.

The relative expression levels of OsDN-LTP8 gene in leaves of different transgenic rice lines were determined by real-time PCR analyses. The base level of expression in ZH11-TC was set at 1.00, and the expression levels in other OsDN-LTP8 lines ranged from about 15-915-fold increases compared to ZH11-TC. ZH11-TC is tissue cultured ZH11 rice. The primers for real-time RT-PCR for the OsDN-LTP8 gene in the transgenic rice are listed below:

```
DP0749-F1:
                                  (SEQ ID NO: 26)
5-ACCAGTGAAGAGAAAGGCG-3'

DP0749-R1:
                                  (SEQ ID NO: 27)
5'-CTTGACATTTGCGAACTGGC-3'
```

The relative expression levels of OsFBX25 gene in leaves of different transgenic rice lines were determined by real-time PCR analyses and ranged from about 657-2128 as compared to the base expression level in ZH111-TC (control; set at 1.00). OsFBX25 over-expressed in all the transgenic lines.

```
DP0963-F1:
                                  (SEQ ID NO: 28)
5'-AGTTGACGGTTGCCCAATAG-3'

DP0963-R1:
                                  (SEQ ID NO: 29)
5'-GTAGATGAAGATGGCCCGAG-3'
```

The relative expression levels of OsGH17 gene in leaves of different transgenic rice lines were determined by real-time PCR analyses and ranged from about 3408-11266 as compared to the base expression level in DP0158 (control; set at 1.00). DP0158 is empty vector transformed ZH11 rice plants. OsGH17 over-expressed in almost all the transgenic lines.

```
DP0979-F1:
                                  (SEQ ID NO: 30)
5'-GAATCTGAGACAGGAACGACAG-3'

DP0979-R1:
                                  (SEQ ID NO: 31)
5'-ATCTCGGTGACTTTGCTCG-3'
```

The relative expression levels of OsDN-LTP9 gene in leaves of different transgenic rice lines were determined by real-time PCR analyses and ranged from about 253-1252 as compared to the base expression level in ZH11-TC (control; set at 1.00). The expression levels in all the tested OsDN-LTP9 lines are higher than that in ZH11-TC seedlings.

```
DP1154-F1:
                                        (SEQ ID NO: 32)
5'-TTCATCTCCACTTCCCAACAC-3'

DP1154-R1:
                                        (SEQ ID NO: 33)
5'-CAGCAACCTGTGTCAAGAAAC-3'
```

Example 4

Greenhouse NUE Screening of Transgenic Rice Plants

For the greenhouse assays, two types of lamps are provided as light source, i.e. sodium lamp and metal halide lamp, and the ratio is 1:1. Lamps provide the 16 h/8 h period of day/night and are placed approximately 1.5 m above the seedbed. The light intensity 30 cm above the seedbed is measured as 10,000-20,000 1× in sunny day, while 6,000-10,000 1× in cloudy day, the relative humidity ranges from 30% to 90%, and the temperature ranges from 20 to 35° C.

NUE Screening Method:

Transgenic T2 seeds and control seeds were sterilized by 800 ppm carbendazol for 8 h at 32° C. and washed 3-5 times, then soaked in water for 16 h at 32° C., germinated for 18 h at 35-37° C. in an incubator. The germinated seeds were selected and planted in pots filled with vermiculite. Randomized block design was used in this trait screening. Every screen unit has 6 blocks which includes one or two controls (ZH11-TC and/or DP0158) and 9-12 transgenic lines. 12 seedlings of each transgenic line were planted in 6 pots located in different positions of the 6 blocks.

After culture for 7-10 days, water was replaced by modified Hoagland solution containing 0.75 mM nitrogen ($KNO_3$) (Table 4). To make an aerobic condition, the nutrition solution was drained off every Monday, Wednesday, and Friday for 2-3 h, and then new modified Hoagland containing low nitrogen solution was added. After culture in low nitrogen solution for 35-40 days, tiller (including the stem and all tillers) numbers were counted, SPAD value was measured by a SPAD meter (SPAD 502 Plus, made by KONICA MINOLTA) at three different positions of the second leaf from the top, and the SPAD value was the average of three readings; and, the fresh weight of the seedlings (cutting from the joint of root and stem) was measured by one percent of the balance. After statistical analysis of these data (tiller number, SPAD value and fresh weight), the positive lines were selected by a cut-off of $P<0.05$.

TABLE 4

| Modified Hoagland's nutrient solution for culturing rice | |
|---|---|
| Molecular formula | Mass concentration(g/L) |
| $KH_2PO_4$ | 34.38 |
| $MgSO_4 \cdot 7H_2O$ | 246.50 |
| $CaCl_2 \cdot 2H_2O$ | 146.88 |
| KCl | 242.29 |
| $KNO_3$ | 101.00 |
| $Na_2SiO_3 \cdot 9H_2O$ | 142.00 |
| $H_3BO_3$ | 1.85 |
| $MnCl_2 \cdot 4H_2O$ | 1.98 |
| $ZnSO_4 \cdot 7H_2O$ | 2.87 |
| $CuSO_4 \cdot 5H_2O$ | 0.25 |
| $(NH_4)_6Mo_7O_{24} \cdot 2H_2O$ | 0.24 |
| EDTA-2Na | 7.45 |
| $FeSO_4 \cdot 7H_2O$ | 5.57 |

NUE Screening Results

1) Validation Results for OsCYP76M5 (DP0788) Transgenic Rice

For OsCYP76M5 transgenic rice plants, eight transgenic lines were tested, ZH11-TC seedlings were used as controls. As shown in Table 5, five lines had significantly greater SPAD values than ZH11-TC control and three lines had significantly greater fresh weights than ZH11-TC control. These results demonstrate that the OsCYP76M5 transgenic rice plants may have enhanced low nitrogen tolerance or improved NUE.

TABLE 5

Low nitrogen assay of OsCYP76M5 transgenic rice plants under greenhouse low nitrogen conditions

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0788 (Construct) | 1.2 | 0.0573 | | 32.39 | 0.0490 | Y | 3.392 | 0.0405 | Y |
| ZH11-TC | 1.0 | | | 30.61 | | | 2.971 | | |
| DP0788.03 | 1.2 | 0.0676 | | 30.26 | 0.7285 | | 3.232 | 0.2782 | |
| DP0788.04 | 1.2 | 0.0676 | | 34.05 | 0.0006 | Y | 3.747 | 0.0012 | Y |
| DP0788.10 | 1.2 | 0.0371 | Y | 32.80 | 0.0286 | Y | 3.547 | 0.0166 | Y |
| DP0788.12 | 1.2 | 0.0815 | | 33.49 | 0.0041 | Y | 3.649 | 0.0048 | Y |
| DP0788.13 | 1.1 | 0.1374 | | 30.63 | 0.9842 | | 2.913 | 0.8073 | |
| DP0788.14 | 1.1 | 0.1615 | | 31.43 | 0.4098 | | 3.267 | 0.2181 | |
| DP0788.15 | 1.2 | 0.0815 | | 32.75 | 0.0331 | Y | 3.350 | 0.1150 | |
| DP0788.18 | 1.2 | 0.0676 | | 33.68 | 0.0022 | Y | 3.435 | 0.0537 | |

2) Validation Results for OsFBX25 (DP0963) Transgenic Rice

For OsFBX25 transgenic rice, ten transgenic lines were tested and ZH11-TC and DP0158 seedlings were used as controls. When the seedlings grew to 3-leaf stage, Hoagland solution containing 0.75 mM potassium nitrate was applied to these plants for 40 days. The average tiller numbers and the fresh weights were greater than ZH11-TC and DP0158 controls. As shown in Table 6, two transgenic lines had significantly more tiller, four transgenic lines had significantly greater SPAD value and fresh weights than ZH11-TC control. As shown in Table 7, three transgenic lines had significantly more tiller, four transgenic lines had significantly greater fresh weights than ZH11-TC control. These results indicate that the OsFBX25 transgenic rice plants had enhanced low nitrogen tolerance or improved NUE.

3) Validation Results for OsGH17 (DP0979) Transgenic Rice

Ten OsGH17 transgenic lines were tested, ZH11-TC seedlings were used as controls, and randomized block design was used. When the rice plants grew to 3-leaf stage, Hoagland solution containing 0.75 mM potassium nitrate was applied to these plants. After low nitrogen stressed for 28 days, tiller number, SPAD value and fresh weight were measured. The average SPAD value and fresh weight of the OsGH17 transgenic rice were more than that of ZH11-TC control. Eight transgenic lines exhibited significantly greater SPAD values and fresh weights than ZH11-TC control (Table 8). These results demonstrate OsGH17 transgenic rice obtained enhanced low nitrogen tolerance or improved NUE, and over-expression of OsGH17 plays a role in enhancing NUE.

TABLE 6

Low nitrogen assay of OsFBX25 transgenic rice plants under greenhouse low nitrogen conditions (ZH11-TC used as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0963 (Construct) | 2.2 | 0.2331 | | 35.97 | 0.0516 | | 3.521 | 0.0659 | |
| ZH11-TC | 1.8 | | | 34.02 | | | 2.983 | | |
| DP0963.01 | 2.4 | 0.1410 | | 36.07 | 0.0693 | | 3.190 | 0.5247 | |
| DP0963.02 | 1.8 | 0.8318 | | 35.27 | 0.2677 | | 3.439 | 0.1619 | |
| DP0963.04 | 2.2 | 0.2563 | | 36.29 | 0.0444 | Y | 3.707 | 0.0265 | Y |
| DP0963.05 | 2.2 | 0.3337 | | 37.66 | 0.0012 | Y | 3.816 | 0.0107 | Y |
| DP0963.08 | 1.8 | 0.8318 | | 35.29 | 0.2606 | | 3.439 | 0.1619 | |
| DP0963.10 | 2.8 | 0.0080 | Y | 38.25 | 0.0002 | Y | 4.306 | 0.0001 | Y |
| DP0963.12 | 2.4 | 0.1009 | | 36.37 | 0.0373 | Y | 3.558 | 0.0779 | |
| DP0963.13 | 2.6 | 0.0319 | Y | 35.38 | 0.2270 | | 3.729 | 0.0224 | Y |
| DP0963.15 | 2.3 | 0.1924 | | 33.93 | 0.9397 | | 2.913 | 0.8324 | |
| DP0963.16 | 1.7 | 0.7033 | | 35.17 | 0.3078 | | 3.115 | 0.6859 | |

TABLE 7

Low nitrogen assay of OsFBX25 transgenic rice plants under greenhouse low nitrogen conditions (DP0158 used as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0963 (Construct) | 2.2 | 0.0850 | | 35.97 | 0.2375 | | 3.521 | 0.0580 | |
| DP0158 | 1.7 | | | 34.78 | | | 2.966 | | |
| DP0963.01 | 2.4 | 0.0525 | | 36.07 | 0.2554 | | 3.190 | 0.4920 | |
| DP0963.02 | 1.8 | 0.7990 | | 35.27 | 0.6679 | | 3.439 | 0.1472 | |
| DP0963.04 | 2.2 | 0.1091 | | 36.29 | 0.1832 | | 3.707 | 0.0232 | Y |
| DP0963.05 | 2.2 | 0.1517 | | 37.66 | 0.0107 | Y | 3.816 | 0.0093 | Y |
| DP0963.08 | 1.8 | 0.7990 | | 35.29 | 0.6559 | | 3.439 | 0.1472 | |
| DP0963.10 | 2.8 | 0.0018 | Y | 38.25 | 0.0021 | Y | 4.306 | 0.0000 | Y |
| DP0963.12 | 2.4 | 0.0351 | Y | 36.37 | 0.1607 | | 3.558 | 0.0697 | |
| DP0963.13 | 2.6 | 0.0090 | Y | 35.38 | 0.5971 | | 3.729 | 0.0195 | Y |
| DP0963.15 | 2.3 | 0.0766 | | 33.93 | 0.4502 | | 2.913 | 0.8724 | |
| DP0963.16 | 1.7 | 0.9313 | | 35.17 | 0.7335 | | 3.115 | 0.6488 | |

TABLE 8

Low nitrogen assay of OsGH17 transgenic rice plants under greenhouse low nitrogen conditions (ZH11-TC as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0979 (Construct) | 1.2 | 0.1383 | | 39.46 | 0.0050 | Y | 4.098 | 0.0465 | Y |
| ZH11-TC | 1.0 | | | 37.17 | | | 3.524 | | |
| DP0979.03 | 1.3 | 0.1258 | | 39.11 | 0.0344 | Y | 4.098 | 0.0465 | Y |
| DP0979.04 | 1.2 | 0.1807 | | 39.79 | 0.0042 | Y | 4.098 | 0.0465 | Y |
| DP0979.07 | 1.2 | 0.3403 | | 40.11 | 0.0013 | Y | 4.098 | 0.0465 | Y |
| DP0979.09 | 1.2 | 0.3403 | | 38.94 | 0.0539 | | 4.098 | 0.0465 | Y |
| DP0979.10 | 1.2 | 0.2518 | | 39.40 | 0.0151 | Y | 4.098 | 0.0465 | Y |
| DP0979.11 | 1.5 | 0.0127 | Y | 40.02 | 0.0019 | Y | 4.098 | 0.0465 | Y |
| DP0979.13 | 1.2 | 0.1807 | | 39.59 | 0.0083 | Y | 4.098 | 0.0465 | Y |
| DP0979.14 | 1.2 | 0.1807 | | 39.18 | 0.0286 | Y | 4.098 | 0.0465 | Y |
| DP0979.15 | 1.2 | 0.2518 | | 39.50 | 0.0111 | Y | 4.098 | 0.0465 | Y |
| DP0979.16 | 1.2 | 0.3403 | | 38.96 | 0.0507 | | 4.098 | 0.0465 | Y |

Example 5

Laboratory Chlorate Screening of Transgenic Rice Plants

Nitrate is a major source of inorganic nitrogen utilized by higher plants. Chlorate is a nitrate analog which can be uptake, transported by the same system with nitrogen and reduced to a toxic compound (chlorite) by nitrate reductase (NR) in plants. To further confirm the nitrogen use efficiency, chlorate solution is selected to treat seedlings, and seedlings which are sensitive to chlorate will be considered to have better nitrogen use efficiency or low nitrogen tolerance.

Laboratory Chlorate Screening Method:

Ten transgenic lines were selected and screened by chlorate solution. ZH11-TC and empty vector (DP0158) transgenic plants were used as controls.

T2 transgenic seeds and control seeds were sterilized and germinated as described in Example 4, and this assay was performed in a culture room kept temperature at 28-30° C. and humidity around ~30%. The germinated seeds were placed in a tube with a hole at the bottom, and water cultured at 30° C. for 6 days till one-leaf and one-terminal bud stage. Uniform seedlings about 5.5 cm in height were selected for chlorate screening. Randomized block design was used in this experiment. There are five blocks in one screened container. Each transgenic line was placed in one row (12 plants/line), and ZH11-TC and DP0158 seedlings were placed in 3 rows (3*12 plants) randomly in one block. Then the seedlings were treated with 0.4 mM chlorate in concentration for 3-5 days at 10 h day/14 h night, the treated seedlings first encountered night and uptake the chlorate solution which was changed in the third day. After treated for 3-5 days, the seedlings were then cultured in 1/10 Hoagland's solution (Table 6) for 4 days. The seedlings with withered leaves and totally without green are counted as sensitive; while the seedlings only with necrosed leaves or stem, or bleached leaves are not considered to be sensitive seedlings.

Sensitive rate was used as a parameter to for this screen, which is the percentage of the number of sensitive plants over the total plant number.

The data was analyzed at construct level (all transgenic plants compared to the control) and transgenic line level (different transgenic lines compared to the control) using a statistic model of "Y~seg+line (seg)+rep+error", with random effect: "rep"; Statistic Method: "SAS Proc Glimmix".

Chlorate Screening Results:

1) Validation Results for OsDN-LTP8 (DP0749) Transgenic Rice

In the first experiment, for OsDN-LTP8 transgenic rice, were treated with 0.8 mM chlorate solution for 5 days and cultured in 1/10 Hoagland solution for 4 days, 235 of the 480 transgenic seedlings (49%) died, while only 60 of the 300 (20%) ZH11-TC seedlings died, and 52 of the 180 (29%) DP0158 seedlings died. The sensitive rate of OsDN-LTP8 transgenic seedlings was significantly higher than both ZH11-TC and DP0158 controls. These results indicate that the OsDN-LTP8 transgenic seedlings have an enhanced chlorate sensitive rate compared to ZH11-TC and DP0158 seedlings at construct level. Table 9 shows the analysis at transgenic line level. Six lines exhibited significantly higher sensitive rates than both of ZH11-TC and DP0158 controls.

TABLE 9

Chlorate sensitive assay of OsDN-LTP8 transgenic rice seedlings at transgenic line level (1st experiment)

| Line ID | Number of dead seedlings | Number of total seedlings | Sensitive rate (%) | CK = ZH11-TC | | CK = DP0158 | |
|---|---|---|---|---|---|---|---|
| | | | | P value | P ≤ 0.05 | P value | P ≤ 0.05 |
| DP0749 (Construct) | 235 | 480 | 49 | 0.0000 | Y | 0.0000 | Y |
| ZH11-TC | 60 | 300 | 20 | | | | |
| DP0158 | 52 | 180 | 29 | | | | |
| DP0749.01 | 38 | 60 | 63 | 0.0000 | Y | 0.0000 | Y |
| DP0749.02 | 31 | 60 | 52 | 0.0000 | Y | 0.0024 | Y |
| DP0749.03 | 39 | 60 | 65 | 0.0000 | Y | 0.0000 | Y |
| DP0749.04 | 18 | 60 | 30 | 0.0933 | | 0.8702 | |
| DP0749.06 | 32 | 60 | 53 | 0.0000 | Y | 0.0012 | Y |
| DP0749.08 | 34 | 60 | 57 | 0.0000 | Y | 0.0003 | Y |
| DP0749.10 | 27 | 60 | 45 | 0.0002 | Y | 0.0259 | Y |
| DP0749.12 | 16 | 60 | 27 | 0.2544 | | 0.7415 | |

The same eight transgenic lines were tested again. 251 of the 480 (52%) OsDN-LTP8 transgenic rice died after chlorate treatment, while 88 of 300 (29%) ZH11-TC seedlings died and 62 of 180 (34%) DP0158 seedlings died. The sensitive rate of OsDN-LTP8 transgenic seedlings was significantly higher than ZH11-TC and DP0158 controls. Further analysis at transgenic line level indicated all the eight transgenic lines showed significantly higher sensitive rates than ZH11-TC seedlings and four transgenic lines showed significantly higher sensitive rates than DP0158 seedling (Table 10). These results demonstrate that OsDN-LTP8 transgenic rice plants exhibited enhanced chlorate sensitive compared to ZH11-TC and DP0158 seedlings at construct and transgenic line level at seedling stages. OsDN-LTP8 transgenic rice are considered to have better nitrogen use efficiency or low nitrogen tolerance, as increased expression of OsDN-LTP8 increased the chlorate sensitivity of transgenic plants and may increase the nitrogen use efficiency or low nitrogen tolerance of transgenic plants.

TABLE 10

Chlorate sensitive assay of OsDN-LTP8 transgenic rice seedlings at transgenic line level ($2^{nd}$ experiment)

| Line ID | Number of dead seedlings | Number of total seedlings | Sensitive rate (%) | CK = ZH11-TC | | CK = DP0158 | |
|---|---|---|---|---|---|---|---|
| | | | | P value | P ≤ 0.05 | P value | P ≤ 0.05 |
| DP0749 (Construct) | 251 | 480 | 52 | 0.0000 | Y | 0.0001 | Y |
| ZH11-TC | 88 | 300 | 29 | | | | |
| DP0158 | 62 | 180 | 34 | | | | |
| DP0749.01 | 29 | 60 | 48 | 0.0061 | Y | 0.0600 | |
| DP0749.02 | 34 | 60 | 57 | 0.0002 | Y | 0.0037 | Y |
| DP0749.03 | 30 | 60 | 50 | 0.0032 | Y | 0.0364 | Y |
| DP0749.04 | 28 | 60 | 47 | 0.0117 | Y | 0.0958 | |
| DP0749.06 | 44 | 60 | 73 | 0.0000 | Y | 0.0000 | Y |
| DP0749.08 | 31 | 60 | 52 | 0.0016 | Y | 0.0214 | Y |
| DP0749.10 | 28 | 60 | 47 | 0.0117 | Y | 0.0958 | |
| DP0749.12 | 27 | 60 | 45 | 0.0213 | Y | 0.1470 | |

2) Validation Results of OsFBX25 (DP0963) Transgenic Rice

In the first experiment, 260 of the 600 transgenic seedlings (43%) died, whereas 75 of the 180 (42%) ZH11-TC seedlings died and 59 of the 180 (33%) DP0158 seedlings died. The sensitive rate of the OsFBX25 transgenic seedlings was significantly higher than the DP0158 control. The result indicates that the OsFBX25 transgenic seedlings had enhanced chlorate sensitive rate at construct level.

Further analysis at transgenic line level indicate that six of the ten transgenic lines had higher sensitive rates than ZH11-TC and DP0158 seedlings, and the sensitive rates of five transgenic lines were significantly higher than DP0158 seedlings (Table 11). These results demonstrate that OsFBX25 transgenic rice plants have enhanced chlorate sensitive rates at construct and transgenic line level at seedling stages. OsFBX25 increased the chlorate sensitivity of transgenic plants.

TABLE 11

Chlorate sensitive assay of OsFBX25 transgenic rice seedlings at transgenic line level ($1^{st}$ experiment)

| Line ID | Number of dead seedlings | Number of total seedlings | Sensitive rate (%) | CK = ZH11-TC | | CK = DP0158 | |
|---|---|---|---|---|---|---|---|
| | | | | P value | P ≤ 0.05 | P value | P ≤ 0.05 |
| DP0963 (Construct) | 260 | 600 | 43 | 0.8164 | | 0.0225 | Y |
| ZH11-TC | 75 | 180 | 42 | | | | |
| DP0158 | 59 | 180 | 33 | | | | |
| DP0963.01 | 40 | 60 | 67 | 0.0016 | Y | 0.0000 | Y |
| DP0963.02 | 33 | 60 | 55 | 0.0781 | | 0.0036 | Y |
| DP0963.04 | 30 | 60 | 50 | 0.2644 | | 0.0207 | Y |
| DP0963.05 | 29 | 60 | 48 | 0.3703 | | 0.0353 | Y |
| DP0963.08 | 14 | 60 | 23 | 0.0147 | | 0.1752 | |
| DP0963.10 | 19 | 60 | 32 | 0.1753 | | 0.8739 | |
| DP0963.12 | 23 | 60 | 38 | 0.6504 | | 0.4351 | |
| DP0963.13 | 27 | 60 | 45 | 0.6523 | | 0.0934 | |
| DP0963.15 | 13 | 60 | 22 | 0.0082 | | 0.1113 | |
| DP0963.16 | 32 | 60 | 53 | 0.1220 | | 0.0066 | Y |

In the second experiment, 500 of the 600 transgenic seedlings (83%) died, whereas 72 of the 180 (40%) ZH11-TC seedlings died and 114 of the 180 (63%) DP0158 seedlings died. The sensitive rate of OsFBX25 transgenic seedlings was significantly higher than ZH11-TC and DP0158 controls. Analysis at transgenic line level indicates that nine of the ten transgenic lines had significantly higher sensitive rates than ZH11-TC and DP0158 seedlings (Table 12). These results further demonstrate that OsFBX25 transgenic rice plants have enhanced chlorate sensitive rates compared to ZH11-TC and DP0158 seedlings at the construct and transgenic line level at seedling stages. Taken together, these results indicate that increased expression of OsFBX25 increased the chlorate sensitivity of transgenic plants and may increase the nitrogen use efficiency or low nitrogen tolerance of transgenic plants.

TABLE 12

Chlorate sensitive assay of OsFBX25 transgenic rice seedlings at transgenic line level ($2^{nd}$ experiment)

| Line ID | Number of dead seedlings | Number of total seedlings | Sensitive rate (%) | CK = ZH11-TC | | CK = DP0158 | |
|---|---|---|---|---|---|---|---|
| | | | | P value | P ≤ 0.05 | P value | P ≤ 0.05 |
| DP0963 (Construct) | 500 | 600 | 83 | 0.0000 | Y | 0.0000 | Y |
| ZH11-TC | 72 | 180 | 40 | | | | |
| DP0158 | 114 | 180 | 63 | | | | |
| DP0963.01 | 42 | 60 | 70 | 0.0002 | Y | 0.3529 | |
| DP0963.02 | 48 | 60 | 80 | 0.0000 | Y | 0.0221 | Y |
| DP0963.04 | 51 | 60 | 85 | 0.0000 | Y | 0.0036 | Y |
| DP0963.05 | 55 | 60 | 92 | 0.0000 | Y | 0.0004 | Y |
| DP0963.08 | 59 | 60 | 98 | 0.0000 | Y | 0.0010 | Y |
| DP0963.10 | 49 | 60 | 82 | 0.0000 | Y | 0.0123 | Y |
| DP0963.12 | 48 | 60 | 80 | 0.0000 | Y | 0.0221 | Y |
| DP0963.13 | 48 | 60 | 80 | 0.0000 | Y | 0.0221 | Y |
| DP0963.15 | 52 | 60 | 87 | 0.0000 | Y | 0.0019 | Y |
| DP0963.16 | 48 | 60 | 80 | 0.0000 | Y | 0.0221 | Y |

3) Validation Results of OsGH17 (DP0979) Transgenic Rice

In the first experiment, 400 of the 600 (67%) OsGH17 transgenic seedlings died, while 117 of the 180 (65%)

ZH11-TC seedlings died and 78 of the 180 (43%) DP0158 seedlings died. The sensitive rate of OsGH17 transgenic seedlings was significantly higher than that of DP0158 control, indicating the OsGH17 transgenic seedlings had increased chlorate sensitivity. Further analysis at transgenic line level demonstrates that eight of the ten transgenic lines had higher sensitive rates than DP0158 seedlings control (Table 13). These results demonstrate that OsGH17 transgenic rice plants had enhanced chlorate sensitivity compared to DP0158 seedlings at construct level and transgenic line level at seedling stages. Increased expression of OsGH17 increased the chlorate sensitivity of transgenic plants.

TABLE 13

Chlorate sensitive assay of OsGH17 rice seedlings at transgenic line level (1$^{st}$ experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0979 (Construct) | 400 | 600 | 67 | 0.6015 | | 0.0000 | Y |
| ZH11-TC | 117 | 180 | 65 | | | | |
| DP0158 | 78 | 180 | 43 | | | | |
| DP0979.03 | 38 | 60 | 63 | 0.8159 | | 0.0101 | Y |
| DP0979.04 | 44 | 60 | 73 | 0.2402 | | 0.0002 | Y |
| DP0979.07 | 34 | 60 | 57 | 0.2525 | | 0.0792 | |
| DP0979.09 | 46 | 60 | 77 | 0.1010 | | 0.0000 | Y |
| DP0979.10 | 40 | 60 | 67 | 0.8149 | | 0.0031 | Y |
| DP0979.11 | 37 | 60 | 62 | 0.6427 | | 0.0176 | Y |
| DP0979.13 | 40 | 60 | 67 | 0.8149 | | 0.0031 | Y |
| DP0979.14 | 47 | 60 | 78 | 0.0616 | | 0.0000 | Y |
| DP0979.15 | 41 | 60 | 68 | 0.6391 | | 0.0016 | Y |
| DP0979.16 | 33 | 60 | 55 | 0.1720 | | 0.1229 | |

In the second experiment, 305 of the 600 (51%) OsGH17 transgenic seedlings died, while 75 of the 180 (42%) ZH11-TC seedlings died and 68 of the 180 (38%) DP0158 seedlings died. The sensitive rate of OsGH17 transgenic seedlings was significantly higher than ZH11-TC and DP0158 controls. Analysis at transgenic line level demonstrates that eight transgenic lines exhibited higher sensitive rates than both DP0158 and ZH11-TC controls (Table 14). These results demonstrate that OsGH17 transgenic rice plants had Taken together, these results demonstrate that increased expression of OsGH17 increased the chlorate sensitivity of transgenic plants and may increase the nitrogen use efficiency or low nitrogen tolerance of transgenic plants.

TABLE 14

Chlorate sensitive assay of OsGH17 rice seedlings at transgenic line level (2$^{nd}$ experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0979 (Construct) | 305 | 600 | 51 | 0.0334 | Y | 0.0031 | Y |
| ZH11-TC | 75 | 180 | 42 | | | | |
| DP0158 | 68 | 180 | 38 | | | | |
| DP0979.03 | 21 | 60 | 35 | 0.3660 | | 0.7020 | |
| DP0979.04 | 27 | 60 | 45 | 0.6527 | | 0.3262 | |

TABLE 14-continued

Chlorate sensitive assay of OsGH17 rice seedlings at transgenic line level (2$^{nd}$ experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0979.07 | 40 | 60 | 67 | 0.0016 | Y | 0.0003 | Y |
| DP0979.09 | 27 | 60 | 45 | 0.6527 | | 0.3262 | |
| DP0979.10 | 26 | 60 | 43 | 0.8215 | | 0.4481 | |
| DP0979.11 | 26 | 60 | 43 | 0.8215 | | 0.4481 | |
| DP0979.13 | 23 | 60 | 38 | 0.6513 | | 0.9382 | |
| DP0979.14 | 41 | 60 | 68 | 0.0009 | Y | 0.0002 | Y |
| DP0979.15 | 41 | 60 | 68 | 0.0009 | Y | 0.0002 | Y |
| DP0979.16 | 33 | 60 | 55 | 0.0786 | | 0.0236 | Y |

4) Validation Results of OsDN-LTP9 (DP1154) Transgenic Rice

In the first experiment, 196 of the 600 (33%) OsDN-LTP9 transgenic seedlings died, while 49 of the 180 (27%) ZH11-TC seedlings and 41 of the 180 (23%) DP0158 seedlings died. The sensitive rate of OsDN-LTP9 transgenic seedlings was significantly higher than DP0158 control and higher than ZH11-TC control, indicating the OsDN-LTP9 transgenic seedlings had increased chlorate sensitivity. Further analysis at transgenic line level demonstrates that six of the ten transgenic lines had higher sensitive rates than ZH11-TC and DP0158 controls (Table 15). These results demonstrate that OsDN-LTP9 transgenic rice plants had enhanced chlorate sensitivity compared to both ZH11-TC and DP0158 seedlings at construct and transgenic line level at seedling stages.

TABLE 15

Chlorate sensitive assay of OsDN-LTP9 rice seedlings at transgenic line level (1$^{st}$ experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP1154 (Construct) | 196 | 600 | 33 | 0.3088 | | 0.0337 | Y |
| ZH11-TC | 49 | 180 | 27 | | | | |
| DP0158 | 41 | 180 | 23 | | | | |
| DP1154.01 | 44 | 60 | 73 | 0.0000 | Y | 0.0000 | Y |
| DP1154.02 | 10 | 60 | 17 | 0.1054 | | 0.3180 | |
| DP1154.03 | 12 | 60 | 20 | 0.2675 | | 0.6522 | |
| DP1154.04 | 19 | 60 | 32 | 0.5066 | | 0.1712 | |
| DP1154.06 | 25 | 60 | 42 | 0.0393 | Y | 0.0063 | Y |
| DP1154.08 | 14 | 60 | 23 | 0.5518 | | 0.9291 | |
| DP1154.09 | 25 | 60 | 42 | 0.0393 | Y | 0.0063 | Y |
| DP1154.12 | 17 | 60 | 28 | 0.8666 | | 0.3839 | |
| DP1154.13 | 21 | 60 | 35 | 0.2517 | | 0.0651 | |
| DP1154.14 | 9 | 60 | 15 | 0.0616 | | 0.2032 | |

In the second experiment, 380 of the 600 (63%) OsDN-LTP9 transgenic seedlings died, while 64 of the 180 (36%) ZH11-TC seedlings died and 87 of the 180 (48%) DP0158 seedlings died. The sensitive rate of OsDN-LTP9 transgenic seedlings was significantly higher than ZH11-TC and DP0158 controls. These results indicate that the OsDN-LTP9 transgenic seedlings had increased chlorate sensitivity. Analysis at the transgenic line level demonstrates that nine transgenic lines exhibited significantly higher sensitive rates than ZH11-TC control and five lines exhibited significantly higher sensitive rates than DP0158 control (Table 16). These results further demonstrate that OsDN-LTP9 transgenic rice plants have enhanced chlorate sensitivity compared to both ZH11-TC and DP0158 seedlings at construct and transgenic line level at seedling stages. These results demonstrate that increased expression of OsDN-LTP9 increased the chlorate sensitivity of transgenic plants and may increase the nitrogen use efficiency or low nitrogen tolerance of transgenic plants.

TABLE 16

Chlorate sensitive assay of OsDN-LTP9 rice seedlings at transgenic line level ($2^{nd}$ experiment)

| Line ID | Number of dead seedlings | Number of total seedlings | Sensitive rate (%) | CK = ZH11-TC | | CK = DP0158 | |
|---|---|---|---|---|---|---|---|
| | | | | P value | P ≤ 0.05 | P value | P ≤ 0.05 |
| DP1154 (Construct) | 380 | 600 | 63 | 0.0000 | Y | 0.0004 | Y |
| ZH11-TC | 64 | 180 | 36 | | | | |
| DP0158 | 87 | 180 | 48 | | | | |
| DP1154.01 | 37 | 60 | 62 | 0.0009 | Y | 0.0798 | |
| DP1154.02 | 35 | 60 | 58 | 0.0033 | Y | 0.1856 | |
| DP1154.03 | 44 | 60 | 73 | 0.0000 | Y | 0.0016 | Y |
| DP1154.04 | 40 | 60 | 67 | 0.0001 | Y | 0.0176 | Y |
| DP1154.06 | 36 | 60 | 60 | 0.0017 | Y | 0.1238 | |
| DP1154.08 | 41 | 60 | 68 | 0.0000 | Y | 0.0101 | Y |
| DP1154.09 | 51 | 60 | 85 | 0.0000 | Y | 0.0000 | Y |
| DP1154.12 | 41 | 60 | 68 | 0.0000 | Y | 0.0101 | Y |
| DP1154.13 | 35 | 60 | 58 | 0.0033 | Y | 0.1856 | |
| DP1154.14 | 20 | 60 | 33 | 0.7558 | | 0.0488 | |

Example 6

Field Low Nitrogen Screens of Mature Plants

Field low nitrogen screens were carried out in Beijing. Two nitrogen levels: N-0 (using fertilizer without nitrogen) and N-1 (with normal fertilizer according to the nitrogen content in the soil) were set in this experiment. Seed germination and seedling culturing were performed as described in Example 4. The germinated seeds were planted in a seedbed field. At 3-leaf stage, the seedlings were transplanted into two testing fields, with 4 replicates and 10 plants per replicate for each transgenic line, (the 4 replicates planted in the same block). The ZH11-TC and DP0158 plants were nearby the transgenic lines in the same block and were used as controls in the statistical analysis.

Rice plants were managed by normal practice using pesticides, but applying phosphorous fertilizer and potassium fertilizer for N-0 treatment and normal fertilizer for N-1.

The plant height which is the length from the rice stem base to the end of panicle or the end of the highest leaf was measured at 20 day after heading. Six rice plants in the middle of one rice row were measured and the arithmetic mean of these three values is the plant height of the transgenic rice plant.

At the end of the season, six representative plants of each transgenic line were harvested from the middle of the row per line. The plant height and grain weight data were statistically analyzed using mixed linear model by ASReml program. Positive transgenic lines are selected based on the analysis (P≤0.1).

1) Field NUE Validation Results of OsDN-LTP8 (DP0749) Transgenic Rice

As shown in Table 17, the grain yield of OsDN-LTP8 transgenic rice was 31.07 g per plant, which was greater than that of ZH11-TC and significantly greater than that of DP0158 control under low nitrogen condition at construct level. All the twelve lines showed greater grain yield per plant than ZH11-TC and DP0158, six lines showed significantly greater grain yield per plant than DP0158 control at line level under low nitrogen condition.

As shown in Table 18, OsDN-LTP8 transgenic rice were taller than ZH11-TC and DP0158 seedlings at construct level under low nitrogen condition. Four OsDN-LTP8 transgenic rice lines were significantly taller than ZH11-TC control, and seven lines were significantly taller than DP0158 control at line level under low nitrogen condition. These results show that OsDN-LTP8 transgenic rice may have increased low nitrogen tolerance.

TABLE 17

Grain yield analysis of OsDN-LTP8 transgenic rice under field low nitrogen condition ($1^{st}$ experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0749 (Construct) | | | 31.07 | 1.57 | 0.247 | | 3.19 | 0.018 | Y |
| ZH11-TC | 40 | 24 | 29.50 | | | | | | |
| DP0158 | 40 | 24 | 27.88 | | | | | | |
| DP0749.01 | 39 | 24 | 33.06 | 3.56 | 0.063 | Y | 5.18 | 0.007 | Y |
| DP0749.02 | 39 | 24 | 30.18 | 0.68 | 0.723 | | 2.30 | 0.228 | |
| DP0749.03 | 35 | 20 | 32.17 | 2.66 | 0.164 | | 4.29 | 0.025 | Y |
| DP0749.04 | 40 | 24 | 29.97 | 0.47 | 0.807 | | 2.09 | 0.274 | |
| DP0749.05 | 40 | 24 | 29.69 | 0.18 | 0.923 | | 1.81 | 0.344 | |
| DP0749.06 | 40 | 24 | 31.93 | 2.43 | 0.204 | | 4.06 | 0.034 | Y |
| DP0749.07 | 40 | 24 | 31.19 | 1.68 | 0.379 | | 3.31 | 0.084 | Y |
| DP0749.08 | 40 | 24 | 30.44 | 0.94 | 0.622 | | 2.57 | 0.179 | |
| DP0749.09 | 40 | 23 | 31.67 | 2.17 | 0.259 | | 3.79 | 0.048 | Y |
| DP0749.10 | 40 | 24 | 32.13 | 2.63 | 0.169 | | 4.25 | 0.026 | Y |

TABLE 17-continued

Grain yield analysis of OsDN-LTP8 transgenic rice under field low nitrogen condition (1st experiment)

| Line ID | Number of survival plants | Number of harvested plants | Yield per plant (g) | CK = ZH11-TC Diff | CK = ZH11-TC P value | CK = ZH11-TC P ≤ 0.1 | CK = DP0158 Diff | CK = DP0158 P value | CK = DP0158 P ≤ 0.1 |
|---|---|---|---|---|---|---|---|---|---|
| DP0749.11 | 40 | 24 | 29.78 | 0.27 | 0.886 | | 1.90 | 0.320 | |
| DP0749.12 | 40 | 24 | 30.65 | 1.15 | 0.550 | | 2.77 | 0.148 | |

TABLE 18

Plant height analysis of OsDN-LTP8 transgenic rice under field low nitrogen condition (1st experiment)

| Line ID | Number of survival plants | Number of harvested plants | Plant Height (cm) | CK = ZH11-TC P value | CK = ZH11-TC P ≤ 0.1 | CK = DP0158 P value | CK = DP0158 P ≤ 0.1 |
|---|---|---|---|---|---|---|---|
| DP0749 (Construct) | | | 110.14 | 0.469 | | 0.017 | Y |
| ZH11-TC | 40 | 24 | 109.36 | | | | |
| DP0158 | 40 | 24 | 107.58 | | | | |
| DP0749.01 | 39 | 24 | 111.19 | 0.110 | | 0.002 | Y |
| DP0749.02 | 39 | 24 | 113.96 | 0.000 | Y | 0.000 | Y |
| DP0749.03 | 35 | 20 | 107.43 | 0.096 | | 0.899 | |
| DP0749.04 | 40 | 24 | 111.19 | 0.102 | | 0.001 | Y |
| DP0749.05 | 40 | 24 | 111.68 | 0.041 | Y | 0.000 | Y |
| DP0749.06 | 40 | 24 | 108.14 | 0.283 | | 0.619 | |
| DP0749.07 | 40 | 24 | 107.35 | 0.079 | | 0.846 | |
| DP0749.08 | 40 | 24 | 108.48 | 0.443 | | 0.434 | |
| DP0749.09 | 40 | 23 | 108.81 | 0.612 | | 0.261 | |
| DP0749.10 | 40 | 24 | 112.36 | 0.010 | Y | 0.000 | Y |
| DP0749.11 | 40 | 24 | 111.64 | 0.048 | Y | 0.000 | Y |
| DP0749.12 | 40 | 24 | 109.50 | 0.904 | | 0.085 | Y |

Five OsDN-LTP8 transgenic rice lines were chosen and tested with four repeats under low nitrogen condition (N-0), normal nitrogen condition (N-1) and high nitrogen condition (N-2). 50 rice plants from each transgenic line were planted in each repeat. There was no nitrogen fertilizer applied during the whole growth period under N-0. Some nitrogen fertilizer applied according to the nitrogen content in the soil under N-1; and 1.5 times nitrogen fertilizer that applied in N-1 were applied under N-2.

Table 19, 20 and 21 demonstrate that the grain yield per plant of OsDN-LTP8 transgenic rice were greater than ZH11-TC plants under low nitrogen condition, normal nitrogen condition and high nitrogen condition, respectively. These results demonstrate that OsDN-LTP8 transgenic rice plants exhibited enhanced low nitrogen tolerance and/or NUE. OsDN-LTP8 gene can be used to improve low nitrogen tolerance and/or NUE.

TABLE 19

Grain yield analysis of OsDN-LTP8 transgenic rice under field low nitrogen condition (2nd experiment)

| Line ID | Number of survival plants | Number of harvested plants | Yield per plant (g) | Diff | P value | P ≤ 0.1 | Yield change (%) |
|---|---|---|---|---|---|---|---|
| ZH11-TC | 200 | 128 | 24.98 | | | | |
| DP0749.02 | 200 | 128 | 25.84 | 0.86 | 0.442 | | 3 |
| DP0749.05 | 199 | 127 | 25.48 | 0.51 | 0.644 | | 2 |
| DP0749.06 | 199 | 128 | 27.43 | 2.46 | 0.046 | Y | 10 |

TABLE 19-continued

Grain yield analysis of OsDN-LTP8 transgenic rice under field low nitrogen condition (2nd experiment)

| Line ID | Number of survival plants | Number of harvested plants | Yield per plant (g) | Diff | P value | P ≤ 0.1 | Yield change (%) |
|---|---|---|---|---|---|---|---|
| DP0749.07 | 200 | 128 | 27.99 | 3.01 | 0.010 | Y | 12 |
| DP0749.09 | 200 | 128 | 27.27 | 2.30 | 0.048 | Y | 9 |

TABLE 20

Grain yield analysis of OsDN-LTP8 transgenic rice under field normal nitrogen condition

| Line ID | Number of survival plants | Number of harvested plants | Yield per plant (g) | Diff | P value | P ≤ 0.1 | Yield change (%) |
|---|---|---|---|---|---|---|---|
| ZH11-TC | 200 | 128 | 31.46 | | | | |
| DP0749.02 | 200 | 128 | 31.54 | 0.08 | 0.956 | | 0 |
| DP0749.05 | 200 | 127 | 31.99 | 0.53 | 0.695 | | 2 |
| DP0749.06 | 200 | 128 | 34.73 | 3.26 | 0.016 | Y | 10 |
| DP0749.07 | 200 | 128 | 34.46 | 2.99 | 0.026 | Y | 10 |
| DP0749.09 | 200 | 128 | 35.61 | 4.14 | 0.004 | Y | 13 |

TABLE 21

Grain yield analysis of OsDN-LTP8 transgenic rice under field high nitrogen condition

| Line ID | Number of survival plants | Number of harvested plants | Yield per plant (g) | Diff | P value | P ≤ 0.1 | Yield change (%) |
|---|---|---|---|---|---|---|---|
| ZH11-TC | 200 | 128 | 33.67 | | | | |
| DP0749.02 | 190 | 126 | 36.14 | 2.46 | 0.071 | Y | 7 |
| DP0749.05 | 200 | 128 | 33.08 | −0.60 | 0.627 | | −2 |
| DP0749.06 | 200 | 128 | 40.24 | 6.57 | 0.000 | Y | 20 |
| DP0749.07 | 200 | 127 | 36.37 | 2.69 | 0.020 | Y | 8 |
| DP0749.09 | 200 | 128 | 37.27 | 3.60 | 0.009 | Y | 11 |

2) Field NUE Validation Results of OsCYP76M5 (DP0788) Transgenic Rice

Twelve OsCYP76M5 (DP0788) transgenic rice lines, ZH11-TC and DP0158 rice were planted in a field. No nitrogen fertilizer was applied during the whole growth period, but there was no low nitrogen stress according to the nitrogen content in the test field. As shown in Table 22, the grain yield of OsCYP76M5 transgenic rice was greater than that of ZH11-TC and DP0158 controls at construct level. Two lines showed significantly greater grain yield per plant than ZH11-TC control, and one line showed significantly greater grain yield per plant than DP0158 control at line level.

TABLE 22

Grain yield analysis of OsCYP76M5 transgenic rice planted under field normal nitrogen condition

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0788 (Construct) | | | 37.93 | 3.957 | 0.239 | | 1.282 | 0.704 | |
| ZH11-TC | 40 | 24 | 33.97 | | | | | | |
| DP0158 | 40 | 24 | 36.65 | | | | | | |
| DP0788.03 | 40 | 24 | 36.39 | 2.42 | 0.538 | | −0.25 | 0.948 | |
| DP0788.04 | 39 | 23 | 36.01 | 2.04 | 0.599 | | −0.64 | 0.869 | |
| DP0788.05 | 39 | 24 | 37.79 | 3.82 | 0.324 | | 1.15 | 0.767 | |
| DP0788.07 | 40 | 23 | 27.96 | −6.01 | 0.120 | | −8.69 | 0.027 | |
| DP0788.09 | 37 | 24 | 37.89 | 3.92 | 0.324 | | 1.24 | 0.748 | |
| DP0788.10 | 32 | 15 | 40.35 | 6.38 | 0.122 | | 3.71 | 0.370 | |
| DP0788.11 | 39 | 24 | 44.29 | 10.32 | 0.008 | Y | 7.64 | 0.049 | Y |
| DP0788.12 | 38 | 24 | 42.25 | 8.28 | 0.032 | Y | 5.60 | 0.153 | |
| DP0788.13 | 39 | 24 | 38.70 | 4.73 | 0.222 | | 2.05 | 0.597 | |
| DP0788.14 | 39 | 24 | 39.03 | 5.06 | 0.197 | | 2.39 | 0.543 | |
| DP0788.15 | 39 | 23 | 35.64 | 1.67 | 0.666 | | −1.01 | 0.795 | |
| DP0788.18 | 37 | 21 | 38.84 | 4.87 | 0.215 | | 2.19 | 0.586 | |

3) Field NUE Validation Results of OsFBX25 (DP0963) Transgenic Rice

Twelve OsFBX25 transgenic rice lines, ZH11-TC and DP0158 rice were planted in field. No nitrogen fertilizer was applied during the whole growth period, but there was no low nitrogen stress according to the nitrogen content in the test field. As shown in Table 23, the grain yield of OsFBX25 transgenic rice was significantly greater than that of ZH11-TC and DP0158 controls at construct level. Nine lines showed significantly greater grain yield per plant than ZH11-TC control, and five lines showed significantly greater grain yield per plant than DP0158 control at line level.

TABLE 23

Grain yield analysis of OsFBX25 transgenic rice under field normal nitrogen condition (1st experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0963 (Construct) | | | 42.65 | 9.51 | 0.013 | Y | 6.54 | 0.086 | Y |
| ZH11-TC | 39 | 24 | 33.14 | | | | | | |
| DP0158 | 40 | 24 | 36.11 | | | | | | |
| DP0963.01 | 40 | 24 | 40.37 | 7.23 | 0.112 | | 4.26 | 0.348 | |
| DP0963.02 | 33 | 21 | 42.69 | 9.55 | 0.031 | Y | 6.58 | 0.135 | |

TABLE 23-continued

Grain yield analysis of OsFBX25 transgenic rice under field normal nitrogen condition (1st experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0963.04 | 40 | 24 | 45.87 | 12.73 | 0.004 | Y | 9.77 | 0.027 | Y |
| DP0963.05 | 38 | 24 | 44.38 | 11.23 | 0.011 | Y | 8.27 | 0.061 | Y |
| DP0963.08 | 37 | 22 | 50.11 | 16.97 | 0.000 | Y | 14.01 | 0.002 | Y |
| DP0963.09 | 38 | 24 | 45.92 | 12.78 | 0.005 | Y | 9.82 | 0.031 | Y |
| DP0963.10 | 37 | 20 | 34.52 | 1.38 | 0.755 | | −1.59 | 0.719 | |
| DP0963.11 | 40 | 24 | 38.48 | 5.34 | 0.227 | | 2.37 | 0.591 | |
| DP0963.12 | 40 | 22 | 45.27 | 12.13 | 0.006 | Y | 9.16 | 0.038 | Y |
| DP0963.13 | 39 | 24 | 41.78 | 8.64 | 0.049 | Y | 5.68 | 0.197 | |
| DP0963.15 | 40 | 24 | 40.53 | 7.39 | 0.095 | Y | 4.42 | 0.314 | |
| DP0963.16 | 40 | 24 | 41.90 | 8.76 | 0.047 | Y | 5.80 | 0.189 | |

The OsFBX25 transgenic rice lines were tested again. ZH11-TC and DP0158 rice were used as controls. No nitrogen fertilizer was applied during the whole growth period, but there was also no low nitrogen stress in the test field. As shown in Table 24, the grain yield of OsFBX25 transgenic rice was significantly greater than that of DP0158 control and ZH11-TC control at construct level. One line showed significantly greater grain yield per plant than ZH11-TC control, and eight lines showed significantly greater grain yield per plant than DP0158 control at line level.

Five OsFBX25 transgenic rice lines were choose and test with four repeats under low nitrogen condition (N-0), normal nitrogen condition (N-1) and high nitrogen condition (N-2). 50 rice plants from each transgenic line were planted in each repeat. There was no nitrogen fertilizer applied during the whole growth period under N-0. Some nitrogen fertilizer applied according to the nitrogen content in the soil under N-1; and 1.5 times nitrogen fertilizer that applied in N-1 were applied under N-2.

Table 25, 26 and 27 demonstrate that the grain yield per plant of OsFBX25 transgenic rice were greater than ZH11-TC plants under low nitrogen condition, normal nitrogen condition and high nitrogen condition, respectively. These results demonstrate that OsFBX25 transgenic rice plants exhibited enhanced nitrogen use efficiency. OsFBX25 gene can be used to improve low nitrogen tolerance and/or NUE.

TABLE 24

Grain yield analysis of OsFBX25 transgenic rice under field normal nitrogen condition (2nd experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0963 (Construct) | | | 32.06 | 1.98 | 0.299 | | 4.09 | 0.032 | Y |
| ZH11-TC | 40 | 24 | 30.08 | | | | | | |
| DP0158 | 40 | 23 | 27.97 | | | | | | |
| DP0963.01 | 40 | 24 | 31.91 | 1.83 | 0.402 | | 3.94 | 0.071 | Y |
| DP0963.02 | 40 | 22 | 32.78 | 2.70 | 0.215 | | 4.81 | 0.027 | Y |
| DP0963.04 | 40 | 24 | 32.01 | 1.93 | 0.375 | | 4.04 | 0.064 | Y |
| DP0963.05 | 40 | 24 | 29.91 | −0.17 | 0.938 | | 1.94 | 0.374 | |
| DP0963.08 | 40 | 24 | 34.15 | 4.07 | 0.062 | Y | 6.18 | 0.004 | Y |
| DP0963.09 | 40 | 18 | 31.63 | 1.55 | 0.490 | | 3.66 | 0.101 | |
| DP0963.10 | 40 | 24 | 33.25 | 3.17 | 0.147 | | 5.28 | 0.015 | Y |
| DP0963.11 | 40 | 18 | 30.38 | 0.30 | 0.895 | | 2.41 | 0.281 | |
| DP0963.12 | 40 | 24 | 33.19 | 3.11 | 0.154 | | 5.22 | 0.017 | Y |
| DP0963.13 | 40 | 24 | 32.85 | 2.77 | 0.204 | | 4.88 | 0.025 | Y |
| DP0963.15 | 40 | 24 | 30.39 | 0.31 | 0.885 | | 2.42 | 0.267 | |
| DP0963.16 | 40 | 24 | 32.28 | 2.20 | 0.314 | | 4.31 | 0.048 | Y |

TABLE 25

Grain yield analysis of OsFBX25 transgenic rice under field low nitrogen condition

| Line ID | Number of survival plants | Number of harvested plants | Yield per plant (g) | Diff | P value | P ≤ 0.1 | Yield change |
|---|---|---|---|---|---|---|---|
| ZH11-TC | 200 | 128 | 24.98 | | | | |
| DP0963.04 | 200 | 128 | 26.70 | 1.73 | 0.114 | | 7% |
| DP0963.05 | 196 | 128 | 23.93 | −1.05 | 0.403 | | −4% |
| DP0963.08 | 200 | 128 | 29.36 | 4.38 | 0.000 | Y | 18% |
| DP0963.09 | 200 | 128 | 29.30 | 4.32 | 0.000 | Y | 17% |
| DP0963.12 | 200 | 123 | 24.79 | −0.19 | 0.873 | | −1% |

TABLE 26

Grain yield analysis of OsFBX25 transgenic rice under field normal nitrogen condition

| Line ID | Number of survival plants | Number of harvested plants | Yield per plant (g) | Diff | P value | P ≤ 0.1 | Yield change |
|---|---|---|---|---|---|---|---|
| ZH11-TC | 200 | 128 | 31.46 | | | | |
| DP0963.04 | 200 | 126 | 37.68 | 6.22 | 0.000 | Y | 20% |
| DP0963.05 | 200 | 127 | 31.46 | 0.00 | 0.999 | | 0% |
| DP0963.08 | 200 | 127 | 32.95 | 1.49 | 0.268 | | 5% |
| DP0963.09 | 200 | 128 | 35.02 | 3.56 | 0.014 | Y | 11% |
| DP0963.12 | 200 | 125 | 33.69 | 2.22 | 0.120 | | 7% |

TABLE 27

Grain yield analysis of OsFBX25 transgenic rice under field high nitrogen condition

| Line ID | Number of survival plants | Number of harvested plants | Yield per plant (g) | Diff | P value | P ≤ 0.1 | Yield change |
|---|---|---|---|---|---|---|---|
| ZH11-TC | 200 | 128 | 33.67 | | | | |
| DP0963.04 | 200 | 128 | 38.69 | 5.02 | 0.000 | Y | 15% |
| DP0963.05 | 200 | 128 | 37.37 | 3.70 | 0.002 | Y | 11% |
| DP0963.08 | 199 | 127 | 38.96 | 5.29 | 0.000 | Y | 16% |
| DP0963.09 | 200 | 127 | 38.66 | 4.99 | 0.000 | Y | 15% |
| DP0963.12 | 199 | 119 | 39.38 | 5.71 | 0.000 | Y | 17% |

4) Field NUE Validation Results of OsGH17 (DP0979) Transgenic Rice

Twelve OsGH17 transgenic rice lines, ZH11-TC and DP0158 rice were planted in field. No nitrogen fertilizer was applied during the whole growth period, but there was no low nitrogen stress according to the nitrogen content in the test field. As shown in Table 28, the grain yield of OsGH17 transgenic rice was significantly greater than ZH11-TC and greater than DP0158 controls at construct level. Eleven lines showed significantly greater grain yield per plant than ZH11-TC control at line level.

TABLE 28

Grain yield analysis of OsGH17 transgenic rice under field normal nitrogen condition (1st experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0979 (Construct) | | | 41.06 | 9.41 | 0.017 | Y | 2.83 | 0.472 | |
| ZH11-TC | 38 | 23 | 31.65 | | | | | | |
| DP0158 | 40 | 24 | 38.22 | | | | | | |
| DP0979.03 | 40 | 22 | 40.58 | 8.93 | 0.044 | Y | 2.35 | 0.595 | |
| DP0979.04 | 39 | 23 | 41.09 | 9.44 | 0.032 | Y | 2.86 | 0.518 | |
| DP0979.06 | 36 | 23 | 37.87 | 6.22 | 0.161 | | −0.36 | 0.936 | |
| DP0979.07 | 40 | 23 | 41.43 | 9.78 | 0.027 | Y | 3.21 | 0.467 | |
| DP0979.09 | 40 | 24 | 39.85 | 8.20 | 0.063 | Y | 1.62 | 0.713 | |
| DP0979.10 | 40 | 22 | 39.97 | 8.32 | 0.061 | Y | 1.75 | 0.694 | |
| DP0979.11 | 38 | 24 | 41.68 | 10.03 | 0.024 | Y | 3.45 | 0.436 | |
| DP0979.12 | 40 | 23 | 41.70 | 10.05 | 0.024 | Y | 3.48 | 0.433 | |
| DP0979.13 | 39 | 23 | 42.84 | 11.19 | 0.012 | Y | 4.61 | 0.298 | |
| DP0979.14 | 38 | 22 | 41.95 | 10.30 | 0.020 | Y | 3.72 | 0.398 | |
| DP0979.15 | 40 | 19 | 41.50 | 9.85 | 0.027 | Y | 3.27 | 0.458 | |
| DP0979.16 | 39 | 24 | 42.25 | 10.60 | 0.016 | Y | 4.02 | 0.361 | |

The OsGH17 transgenic rice lines were tested again, and ZH11-TC and DP0158 rice were used as control. No nitrogen fertilizer was applied during the whole growth period, but there was also no low nitrogen stress according to the nitrogen content in the test field. As shown in Table 29, the grain yield of OsGH17 transgenic rice was significantly greater than ZH11-TC and greater than DP0158 controls at construct level. All the twelve lines showed significantly greater grain yield per plant than ZH11-TC control at line level.

TABLE 29

Grain yield analysis of OsGH17 transgenic rice under field normal nitrogen condition (2$^{nd}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0979 (Construct) | | | 31.76 | 7.66 | 0.000 | Y | 0.52 | 0.783 | |
| ZH11-TC | 40 | 24 | 24.10 | | | | | | |
| DP0158 | 40 | 24 | 31.23 | | | | | | |
| DP0979.03 | 40 | 24 | 32.46 | 8.37 | 0.000 | Y | 1.23 | 0.571 | |
| DP0979.04 | 39 | 24 | 31.89 | 7.79 | 0.000 | Y | 0.66 | 0.763 | |
| DP0979.06 | 40 | 24 | 31.20 | 7.10 | 0.001 | Y | −0.04 | 0.987 | |
| DP0979.07 | 40 | 24 | 33.06 | 8.96 | 0.000 | Y | 1.83 | 0.401 | |
| DP0979.09 | 40 | 24 | 31.40 | 7.30 | 0.001 | Y | 0.16 | 0.941 | |
| DP0979.10 | 40 | 24 | 32.18 | 8.08 | 0.000 | Y | 0.94 | 0.665 | |
| DP0979.11 | 40 | 24 | 32.31 | 8.21 | 0.000 | Y | 1.07 | 0.623 | |
| DP0979.12 | 40 | 24 | 32.41 | 8.32 | 0.000 | Y | 1.18 | 0.590 | |
| DP0979.13 | 40 | 24 | 31.70 | 7.60 | 0.000 | Y | 0.47 | 0.831 | |
| DP0979.14 | 40 | 24 | 31.21 | 7.11 | 0.001 | Y | −0.03 | 0.990 | |
| DP0979.15 | 40 | 24 | 30.63 | 6.53 | 0.003 | Y | −0.61 | 0.780 | |
| DP0979.16 | 40 | 24 | 30.67 | 6.57 | 0.003 | Y | −0.57 | 0.796 | |

5) Field NUE Validation Results of OsDN-LTP9 (DP1154) Transgenic Rice

Twelve OsDN-LTP9 transgenic rice lines, ZH11-TC and DP0158 rice were planted in field. No nitrogen fertilizer was applied during the whole growth period, but there was no low nitrogen stress according to the nitrogen content in the test field. As shown in Table 30, the grain yield of OsDN-LTP9 transgenic rice was greater than that of ZH11-TC and DP0158 controls at construct level. Six lines showed significantly greater grain yield per plant than DP0158 control at line level.

TABLE 30

Grain yield analysis of OsDN-LTP9 transgenic rice under field normal nitrogen condition (1$^{st}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP1154 (Construct) | | | 48.16 | 0.96 | 0.805 | | 6.07 | 0.119 | |
| ZH11-TC | 39 | 23 | 47.20 | | | | | | |
| DP0158 | 39 | 24 | 42.09 | | | | | | |
| DP1154.01 | 40 | 23 | 46.80 | −0.40 | 0.93 | | 4.71 | 0.30 | |
| DP1154.02 | 38 | 21 | 44.77 | −2.43 | 0.59 | | 2.68 | 0.55 | |
| DP1154.03 | 38 | 21 | 49.64 | 2.44 | 0.59 | | 7.56 | 0.09 | Y |
| DP1154.04 | 38 | 21 | 48.49 | 1.29 | 0.775 | | 6.40 | 0.158 | |
| DP1154.06 | 40 | 24 | 50.27 | 3.07 | 0.497 | | 8.19 | 0.070 | Y |
| DP1154.08 | 39 | 23 | 45.69 | −1.51 | 0.738 | | 3.60 | 0.426 | |
| DP1154.09 | 37 | 16 | 52.47 | 5.27 | 0.246 | | 10.38 | 0.022 | Y |
| DP1154.10 | 38 | 21 | 44.07 | −3.13 | 0.493 | | 1.99 | 0.661 | |
| DP1154.12 | 31 | 21 | 51.38 | 4.18 | 0.355 | | 9.29 | 0.040 | Y |
| DP1154.13 | 35 | 20 | 50.51 | 3.31 | 0.464 | | 8.42 | 0.063 | Y |
| DP1154.14 | 35 | 22 | 50.12 | 2.92 | 0.518 | | 8.03 | 0.077 | Y |
| DP1154.15 | 38 | 21 | 43.69 | −3.51 | 0.440 | | 1.61 | 0.723 | |

The OsDN-LTP9 transgenic rice lines were tested again, and ZH11-TC and DP0158 rice were used as control. No nitrogen fertilizer was applied during the whole growth period, but there was also no low nitrogen stress according to the nitrogen content in the test field. As shown in Table 31, the grain yield of OsDN-LTP9 transgenic rice was greater than ZH11-TC and DP0158 controls at construct level. Four lines showed significantly greater grain yield per plant than ZH11-TC control at line level.

TABLE 31

Grain yield analysis of OsDN-LTP9 transgenic rice under field normal nitrogen condition ($2^{nd}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP1154 (Construct) | | | 29.24 | 2.87 | 0.130 | | 0.73 | 0.703 | |
| ZH11-TC | 40 | 24 | 26.37 | | | | | | |
| DP0158 | 40 | 24 | 28.51 | | | | | | |
| DP1154.01 | 40 | 24 | 28.45 | 2.08 | 0.336 | | −0.07 | 0.976 | |
| DP1154.02 | 40 | 24 | 29.30 | 2.94 | 0.177 | | 0.79 | 0.718 | |
| DP1154.03 | 40 | 24 | 28.45 | 2.08 | 0.338 | | −0.07 | 0.976 | |
| DP1154.04 | 40 | 24 | 28.11 | 1.74 | 0.424 | | −0.41 | 0.853 | |
| DP1154.06 | 40 | 24 | 30.08 | 3.71 | 0.089 | Y | 1.56 | 0.474 | |
| DP1154.08 | 40 | 24 | 30.76 | 4.40 | 0.044 | Y | 2.25 | 0.303 | |
| DP1154.09 | 40 | 24 | 29.01 | 2.64 | 0.222 | | 0.49 | 0.820 | |
| DP1154.10 | 40 | 21 | 27.69 | 1.32 | 0.544 | | −0.82 | 0.706 | |
| DP1154.12 | 40 | 24 | 30.37 | 4.00 | 0.067 | Y | 1.85 | 0.396 | |
| DP1154.13 | 40 | 24 | 29.42 | 3.05 | 0.161 | | 0.91 | 0.678 | |
| DP1154.14 | 40 | 24 | 30.26 | 3.90 | 0.073 | Y | 1.75 | 0.420 | |
| DP1154.15 | 40 | 24 | 29.00 | 2.63 | 0.227 | | 0.48 | 0.824 | |

Five OsDN-LTP9 transgenic rice lines were choose and test with four repeats under low nitrogen condition (N-0), normal nitrogen condition (N-1) and high nitrogen condition (N-2). 50 rice plants from each transgenic line were planted in each repeat. There was no nitrogen fertilizer applied during the whole growth period under N-0. Some nitrogen fertilizer applied according to the nitrogen content in the soil under N-1; and 1.5 times nitrogen fertilizer that applied in N-1 were applied under N-2.

Table 32, 33 and 34 demonstrate that the grain yield per plant of OsDN-LTP9 transgenic rice were greater than ZH11-TC plants under low nitrogen condition, normal nitrogen condition and high nitrogen condition, respectively. These results demonstrate that OsDN-LTP9 transgenic rice plants exhibited enhanced nitrogen use efficiency. OsDN-LTP9 gene can be used to improve low nitrogen tolerance and/or NUE.

TABLE 32

Grain yield analysis of OsDN-LTP9 transgenic rice under field low nitrogen condition

| Line ID | Number of survival plants | Number of harvested plants | Yield per plant (g) | Diff | P value | P ≤ 0.1 | Yield change |
|---|---|---|---|---|---|---|---|
| ZH11-TC | 200 | 128 | 24.98 | | | | |
| DP1154.06 | 195 | 127 | 25.22 | 0.24 | 0.844 | | 1% |
| DP1154.09 | 200 | 128 | 27.73 | 2.75 | 0.020 | Y | 11% |
| DP1154.12 | 200 | 128 | 28.37 | 3.40 | 0.006 | Y | 14% |
| DP1154.13 | 200 | 127 | 30.30 | 5.32 | 0.000 | Y | 21% |
| DP1154.14 | 200 | 126 | 26.73 | 1.76 | 0.145 | | 7% |

TABLE 33

Grain yield analysis of OsDN-LTP9 transgenic rice under field normal nitrogen condition

| Line ID | Number of survival plants | Number of harvested plants | Yield per plant (g) | Diff | P value | P ≤ 0.1 | Yield change |
|---|---|---|---|---|---|---|---|
| ZH11-TC | 200 | 128 | 31.46 | | | | |
| DP1154.06 | 200 | 127 | 33.45 | 1.99 | 0.145 | | 6% |
| DP1154.09 | 199 | 128 | 34.33 | 2.87 | 0.030 | Y | 9% |
| DP1154.12 | 200 | 127 | 35.35 | 3.88 | 0.004 | Y | 12% |
| DP1154.13 | 200 | 127 | 33.80 | 2.34 | 0.084 | Y | 7% |
| DP1154.14 | 200 | 128 | 36.01 | 4.54 | 0.001 | Y | 14% |

TABLE 34

Grain yield analysis of OsDN-LTP9 transgenic rice under field high nitrogen condition

| Line ID | Number of survival plants | Number of harvested plants | Yield per plant (g) | Diff | P value | P ≤ 0.1 | Yield change |
|---|---|---|---|---|---|---|---|
| ZH11-TC | 200 | 128 | 33.67 | | | | |
| DP1154.06 | 200 | 127 | 36.74 | 3.06 | 0.013 | Y | 9% |
| DP1154.09 | 200 | 128 | 35.78 | 2.11 | 0.083 | Y | 6% |
| DP1154.12 | 200 | 128 | 40.04 | 6.37 | 0.000 | Y | 19% |
| DP1154.13 | 200 | 128 | 37.67 | 4.00 | 0.000 | Y | 12% |
| DP1154.14 | 200 | 127 | 35.60 | 1.92 | 0.109 | | 6% |

Example 7

Transformation and Evaluation of Maize with Rice Low Nitrogen Tolerance Genes Maize plants can be transformed with one of the polynucleotides encoding the polypeptides described herein or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter or a tissue-preferred promoter. The recombinant DNA construct can be introduced into maize cells by particle bombardment substantially as described in International Patent Publication WO 2009/006276. Alternatively, maize plants can be transformed with the recombinant DNA construct by *Agrobacterium*-mediated transformation substantially as described by Zhao et al. in *Meth. Mol. Biol.* 318:315-323 (2006) and in Zhao et al., *Mol. Breed.* 8:323-333 (2001) and U.S. Pat. No. 5,981,840 issued Nov. 9, 1999.

Progeny of the regenerated plants, such as T$_1$ plants, can be subjected to a low nitrogen stress. Using image analysis, plant area, volume, growth rate and color can be measured at multiple times before and during low nitrogen stress. Significant delay in leaf area reduction, a reduced yellow-color accumulation, and/or an increased growth rate during low nitrogen stress, relative to a control, will be considered evidence that the gene functions in maize to enhance NUE.

Example 8

Laboratory NUE Screening of Rice Low Nitrogen Tolerance Genes in *Arabidopsis*

To understand whether rice low nitrogen tolerance genes can improve dicot plants' low nitrogen tolerance, or other traits, rice low nitrogen tolerance gene expression vectors can be transformed into *Arabidopsis* (Columbia) using floral dip method by *Agrobacterium* mediated transformation procedure and transgenic plants were identified (Clough, S. T. and Bent, A. F. (1998) *The Plant Journal* 16, 735-743; Zhang, X. et al. (2006) *Nature Protocols* 1: 641-646).

Progeny of the regenerated plants, such as T$_1$ plants, can be subjected to a low nitrogen stress. Using image analysis, plant area, volume, growth rate and color can be measured at multiple times before and during low nitrogen stress. Significant delay in leaf area reduction, a reduced yellow-color accumulation, and/or an increased growth rate during low nitrogen stress, relative to a control, will be considered evidence that the gene functions in *Arabidopsis* to enhance NUE.

---

What is claimed is:

1. A modified plant or modified seed comprising a polynucleotide encoding a polypeptide comprising an amino acid sequence having at least 95% identity to SEQ ID NO: 3 operably linked to at least one heterologous regulatory element, wherein the modified plant or a plant grown from the modified seed has increased expression of the polypeptide and exhibits improved nitrogen stress tolerance or enhanced yield when compared to the control plant.

2. The modified plant or modified seed of claim 1, wherein the modified plant or modified seed comprises in its genome a recombinant DNA construct comprising the polynucleotide operably linked to the at least one heterologous regulatory element.

3. The modified plant or modified seed of claim 1, wherein said modified plant or plant grown from the modified seed is selected from the group consisting of rice, maize, soybean, sunflower, sorghum, canola, wheat, alfalfa, cotton, barley, millet, sugar cane and switchgrass.

4. A method of increasing nitrogen stress tolerance/NUE in a plant, the method comprising:
(a) expressing in a plant a polynucleotide encoding a polypeptide comprising an amino acid sequence having at least 95% identity to SEQ ID NO: 3 operably linked to at least one heterologous regulatory element, wherein the expression level of the polynucleotide is increased compared to that of a control plant; and
(b) selecting a plant of part (a) comprising the polynucleotide operably linked to the regulatory element for increased nitrogen stress tolerance/NUE as compared to a control plant not comprising the polynucleotide operably linked to the at least one heterologous regulatory element.

5. The method of claim 4, wherein part (a) comprises introducing in a regenerable plant cell a recombinant DNA construct comprising the polynucleotide operably linked to the at least one heterologous regulatory element; and (b) generating the plant wherein the plant comprises, in its genome, the recombinant DNA construct.

6. The method of claim 4, wherein part (a) comprises introducing in a regenerable plant cell a targeted genetic modification at a genomic locus comprising an endogenous polynucleotide that encodes the polypeptide having an amino acid sequence of at least 95% sequence identity compared to SEQ ID NO: 3, wherein the targeted genetic modification operably links a heterologous promoter to the endogenous polynucleotide; and (b) generating the plant wherein the level of the polypeptide is increased in the plant.

7. The method of claim 6, wherein the targeted genetic modification is introduced using CRISPR-cas.

8. The method of claim 5, wherein the heterologous regulatory element is a heterologous promoter.

9. The method of claim 4, wherein said plant is selected from the group consisting of rice, maize, soybean, sunflower, sorghum, canola, wheat, alfalfa, cotton, barley, millet, sugar cane and switchgrass.

* * * * *

SEQUENCE LISTING

```
<160> NUMBER OF SEQ ID NOS: 33

<210> SEQ ID NO 1
<211> LENGTH: 2128
<212> TYPE: DNA
<213> ORGANISM: Oryza sativa

<400> SEQUENCE: 1
cattggctaa tttgtaattg gtgctttgca aataatgtca gcggtaagtt atcatttatg      60
tagactccaa aaatgttttg tggggcttat tgctttggaa aatgttctat aaattgtgtt     120
gctgttctag acttagtagt attttatgaa atgtttatgt tgtatggtat agtttgtgct     180
ttttttagtg tgtggcatta catagcactt tataatatag attgctttat aaaaaattga     240
ataaacaaaa aaaatcaaaa tacaagttaa cttgaaaatc tgtaggtgag aagttatgat     300
gatgcttttt taaggcaact gcatcaaagt gtagctcctt caattgtgca actggcagtt     360
ttcaatgcaa aaagtaccca aataccatgc catcttggta ctggattggt attatgtgtg     420
acacccaatt atattggggt aatcacatct atcagttgtg atccgaaaga tggtttcaga     480
gtcgttgcga gatttggtga tcaagaagat ttggagacag aagttgtcag aacaagttca     540
ttactttctg cgttggttgt gcgaggatgt aatgttcagg ccataccttg cattcctaca     600
tcgtttcatg aaggcgactt accagaggca gatgttgttt tttgtattgg atgttttagc     660
attgtgaaag agcagataat gactgcggga ataatcaggt atccatctat tcttgatgac     720
aattcatgga tattttgtt ttgtactgtt acttttgttg catttcattc cccttgtatt     780
atattttgtt ttagtttatg tttaaagtgc ttataagatt tgacggaaga taattgagag     840
gaaaatgcag gccactgaac tttcaaattg caaatttagg ccttcaaact tggttaatgt     900
accatcatag gttcaaaggt gaacatactc cttagggaat agatgtggca tgctaacatg     960
gagtgaactt ggtatgtggg agcacgtgaa cttgccatgg attagaatat atgcatggaa    1020
```

```
cctcctaaaa tcgatatgct ctttactctt gttccacttt actcatgctg taatccccaa    1080
attatgtcgt ctcccgttca caacaccatt ggtctataat cgacgaaatg gtaggacaag    1140
ctagccattt tcaattgcaa tgagttggct tctcctggca tgccattgat tcctggtcat    1200
cgatgagatg aatgatcagc aggttgtttg gtgattatgt tatgagcaat tgggattgat    1260
agtgaacacc aagttgattt tgcatatatt tccatccacg tcaatctcaa ttctcacatt    1320
ctcccacatg ccacaccagc tgcttgcttg ttgacatgca tcataagctc ttagacattt    1380
gatgataaat taaataagtt tgctggctta aatttgcagt ttgaaagttt agagatctgg    1440
acaacacttt atggaatgtt ggtattttat tcttaattat ttattcttta agtatgtcct    1500
tcttaataac agttatttaa tgcatgccag tgtatgcgaa tttgaaaagg aactgagagg    1560
agaacaacag gttagcacat ttgtgcatac ctgtccgatt ggggatgggt tgatgggagc    1620
acctatatgt agtcgattcg gaaaagtttt tggaatgaat gttgctcgga cagcactgtg    1680
ttcatcaatt aattttgccc tgaacaatag tcaattaaag gttgaattgg caaaactatt    1740
acagaatgaa gattatgagg tactaccttt tgtacaaaac ctaaagcccg agtaatagct    1800
tttgctgttt taggtcgtaa aaggctcaga aatttacaga tttttaactt catgataata    1860
ttttatagat gtcagctctt attgagaagt acgattctga aaaaacgagt gcatcgaaga    1920
agagaaaggg aaggggtgtt agcagttcgc aaatgtcaag gtcaccagtg aagagaaagg    1980
cgggtggcag ttcttcgtca agagggaga ggggtgttgc cagttcgcaa atgtcaagtt    2040
taccagcgaa gagaaaggcg ggtggcagtt cttcgtcaag agcgatataa agaggtgtg    2100 tgccacagtt ttctattgtt caccatag                                       2128

<210> SEQ ID NO 2
<211> LENGTH: 873
<212> TYPE: DNA
<213> ORGANISM: Oryza sativa

<400> SEQUENCE: 2
atgtcagcgg tgagaagtta tgatgatgct ttttaaggc aactgcatca aagtgtagct      60
ccttcaattg tgcaactggc agttttcaat gcaaaaagta cccaaatacc atgccatctt    120
ggtactggat tggtattatg tgtgacaccc aattatattg gggtaatcac atctatcagt    180
tgtgatccga agatgggttt cagagtcgtt gcgagatttg gtgatcaaga agatttggag    240
acagaagttg tcagaacaag ttcattactt tctgcgttgg ttgtgcgagg atgtaatgtt    300
caggccatac cttgcattcc tacatcgttt catgaaggcg acttaccaga ggcagatgtt    360
gttttttgta ttggatgttt tagcattgtg aaagagcaga taatgactgc gggaataatc    420
agtgtatgcg aatttgaaaa ggaactgaga ggagaacaac aggttagcac atttgtgcat    480
acctgtccga ttggggatgg gttgatggga gcacctatat gtagtcgatt cggaaaagtt    540
tttggaatga atgttgctcg gacagcactg tgttcatcaa ttaattttgc cctgaacaat    600
agtcaattaa aggttgaatt ggcaaaacta ttacagaatg aagattatga gatgtcagct    660
cttattgaga agtacgattc tgaaaaaacg agtgcatcga agaagagaaa gggaaggggt    720
gttagcagtt cgcaaatgtc aaggtcacca gtgaagagaa aggcgggtgg cagttcttcg    780
tcaagaaggg agagggggtgt tgccagttcg caaatgtcaa gtttaccagc gaagagaaag    840
gcgggtggca gttcttcgtc aagagcgata taa                                 873

<210> SEQ ID NO 3
<211> LENGTH: 290
```

<212> TYPE: PRT
<213> ORGANISM: Oryza sativa

<400> SEQUENCE: 3

```
Met Ser Ala Val Arg Ser Tyr Asp Asp Ala Phe Leu Arg Gln Leu His
1               5                   10                  15

Gln Ser Val Ala Pro Ser Ile Val Gln Leu Ala Val Phe Asn Ala Lys
            20                  25                  30

Ser Thr Gln Ile Pro Cys His Leu Gly Thr Gly Leu Val Leu Cys Val
        35                  40                  45

Thr Pro Asn Tyr Ile Gly Val Ile Thr Ser Ile Ser Cys Asp Pro Lys
    50                  55                  60

Asp Gly Phe Arg Val Val Ala Arg Phe Gly Asp Gln Glu Asp Leu Glu
65                  70                  75                  80

Thr Glu Val Val Arg Thr Ser Ser Leu Leu Ser Ala Leu Val Val Arg
                85                  90                  95

Gly Cys Asn Val Gln Ala Ile Pro Cys Ile Pro Thr Ser Phe His Glu
            100                 105                 110

Gly Asp Leu Pro Glu Ala Asp Val Val Phe Cys Ile Gly Cys Phe Ser
        115                 120                 125

Ile Val Lys Glu Gln Ile Met Thr Ala Gly Ile Ile Ser Val Cys Glu
    130                 135                 140

Phe Glu Lys Glu Leu Arg Gly Glu Gln Gln Val Ser Thr Phe Val His
145                 150                 155                 160

Thr Cys Pro Ile Gly Asp Gly Leu Met Gly Ala Pro Ile Cys Ser Arg
                165                 170                 175

Phe Gly Lys Val Phe Gly Met Asn Val Ala Arg Thr Ala Leu Cys Ser
            180                 185                 190

Ser Ile Asn Phe Ala Leu Asn Asn Ser Gln Leu Lys Val Glu Leu Ala
        195                 200                 205

Lys Leu Leu Gln Asn Glu Asp Tyr Glu Met Ser Ala Leu Ile Glu Lys
    210                 215                 220

Tyr Asp Ser Glu Lys Thr Ser Ala Ser Lys Lys Arg Lys Gly Arg Gly
225                 230                 235                 240

Val Ser Ser Ser Gln Met Ser Arg Ser Pro Val Lys Arg Lys Ala Gly
                245                 250                 255

Gly Ser Ser Ser Arg Arg Glu Arg Gly Val Ala Ser Ser Gln Met
            260                 265                 270

Ser Ser Leu Pro Ala Lys Arg Lys Ala Gly Gly Ser Ser Ser Ser Arg
        275                 280                 285

Ala Ile
    290
```

<210> SEQ ID NO 4
<211> LENGTH: 1728
<212> TYPE: DNA
<213> ORGANISM: Oryza sativa

<400> SEQUENCE: 4

```
gattagctcc atttttccacc taagagtgca ttaatatctc gattgcttgg cagtcatgga      60
ggtgacatcc accccagcga tgctgctcta cgccgccctg ttcgcggcgg cgctgctgta     120
cctcgccgtc gcggtccggc gcggccgcgg cgccggcctg ccgccgggtc gacggggct      180 gccgctcgtc ggcagcttgc tgtccctcga cccggagctg cacacctact cgcggcct      240 cgccgccagg tacggcccca tcttctctat ccgcctcggc tccaagctcg gcgtcgtcgt     300
```

```
cacctcgccg gcgctggcgc gggaggtgct gcgcgaccac gacctcgtct tctccaaccg    360
cgacacgccc gacgccgcgt gctccatctc ctacggcggc gggcagaaca tcgtgtggaa    420
cccggtcggc cccacgtggc gcctcctccg ccgcatctgc gtccacgaga tgatcggccc    480
cgccggcctc gacagcctcc acggcctccg ccgccgggga ttcatggcca cgctccacca    540
cctgcgcgcg cggtccggcg agcccgtcaa cgtcggcgcg cagatgttcc tcaccgtgat    600
gaacgtggtg accggcgcgc tgtgggcgg caacgtcggc agcgagagcg agcggacgac    660
ggtggggaag gagttccggg agctcgtcgc cgacatcacc gagttgctcg cgcgcccaa     720 cgtgtccgac ttcttcccgg cgctggcgcc gctcgacatc cagggcatcc gcaacaagtc    780
cgacctgctc aaggaccgct tcgacgacat cttcgccagg atcatccaga agaggaccga    840
gtccgaccat gccgccgccg ccggcagac ggcgtcggac ttcctcgagt acatgctcaa     900
gctggagaag gaaggcggcg acgggaagac cgccttcacc atgaccaacg tcaaggccct    960
gctcatggta agtgctcact gctcagtcac tgcactgccg cgtcggaga cgacgacacc    1020 accattcatg gctgtgtgat ttggctgcag gacatggtga tcgggggac ggagacgacg     1080 tcgaacaccg tggaatgggg catggcgag atgctccaga acaggggac gctgcgcaag      1140 gtgcgggagg agctcgacgc ggtggtgggg cgcgacggcg tggtggagga gagccacctc    1200
ccgaagctgc actacctgaa tctggtggtc aaggagacgc tccggctgca cccgcgctg    1260 ccgctgatgg tgccgcactg ccccggcgag gacgccacgg tgggcggcca ccgcgtcccg    1320
gcgggcgccc gggtgttcgt caacgtgtgg gcgatccaga gggacccggc ggtgtggaag    1380
gacccggaac acttcatccc ggagaggttc ttgccggcgg acgcggcgg agggcggagg     1440 ctggacttca ccgggagcga gcaggagtac atgccgttcg ggtccgggag gaggatctgc    1500
gccggcgtcg ccatggcgga gcggatggtg gcctactcgc tggcgatgct ggtgcaggcg    1560
ttcgactggg agctgccggc cggcgagcgg ctggacctcg ccgagcggtt cggcatcgtg    1620
atgaagaagg ccacgccgct ggtcgccgtg cccacgccga ggctctccaa ccctcagctc    1680
tactccgcct agataccaaa ggttttaaat ctcgggctat aattgtag                1728
```

<210> SEQ ID NO 5
<211> LENGTH: 1554
<212> TYPE: DNA
<213> ORGANISM: Oryza sativa
<400> SEQUENCE: 5

```
atggaggtga catccacccc agcgatgctg ctctacgccg ccctgttcgc ggcggcgctg     60
ctgtacctcg ccgtcgcggt ccggcgcggc cgcggcgccg gcctgccgcc gggtccgacg    120
gggctgccgc tcgtcggcag cttgctgtcc ctcgacccgg agctgcacac ctacttcgcc    180
ggcctcgccg ccaggtacgg ccccatcttc tctatccgcc tcggctccaa gctcggcgtc    240
gtcgtcacct cgccgcgct ggcgcgggag gtgctgcgcg accacgacct cgtcttctcc     300
aaccgcgaca cgcccgacgc cgcgtgctcc atctcctacg gcggcgggca gaacatcgtg    360
tggaacccgg tcggccccac gtggcgcctc ctccgccgca tctgcgtcca cgagatgatc    420
ggccccgccg gcctcgacag cctccacggc ctccgccgcc gggagttcat ggccacgctc    480
caccacctgc gcgcgcggtc cggcgagccc gtcaacgtcg cgcgcagat gttcctcacc     540 gtgatgaacg tggtgaccgg cgcgctgtgg gcggcaacg tcggcagcga gagcgagcgg    600
acgacggtgg ggaaggagtt ccgggagctc gtcgccgaca tcaccgagtt gctcggcgcg    660
```

```
cccaacgtgt ccgacttctt cccggcgctg gcgccgctcg acatccaggg catccgcaac    720
aagtccgacc tgctcaagga ccgcttcgac gacatcttcg ccaggatcat ccagaagagg    780
accgagtccg accatgccgc cgccgccggc gagacggcgt cggacttcct cgagtacatg    840
ctcaagctgg agaaggaagg cggcgacggg aagaccgcct tcaccatgac caacgtcaag    900
gccctgctca tggacatggt gatcgggggg acggagacga cgtcgaacac cgtggaatgg    960
ggcatggcgg agatgctcca gaacaggggg acgctgcgca aggtgcggga ggagctcgac    1020
gcggtggtgg ggcgcgacgg cgtggtggag gagagccacc tcccgaagct gcactacctg    1080
aatctggtgg tcaaggagac gctccggctg caccoggcgc tgccgctgat ggtgccgcac    1140
tgccccggcg aggacgccac ggtgggcggc caccgcgtcc cggcgggcgc ccgggtgttc    1200
gtcaacgtgt gggcgatcca gagggacccg gcggtgtgga aggacccgga acacttcatc    1260
ccggagaggt tcttgccggc ggacggcggc ggagggcgga ggctggactt caccgggagc    1320
gagcaggagt acatgccgtt cgggtccggg aggaggatct cgccggcgt cgccatggcg    1380 gagcggatgg tggcctactc gctggcgatg ctggtgcagg cgttcgactg ggagctgccg    1440
gccggcgagc ggctggacct cgccgagcgg ttcggcatcg tgatgaagaa ggccacgccg    1500
ctggtcgccg tgcccacgcc gaggctctcc aaccctcagc tctactccgc ctag           1554
```

<210> SEQ ID NO 6
<211> LENGTH: 517
<212> TYPE: PRT
<213> ORGANISM: Oryza sativa

<400> SEQUENCE: 6

```
Met Glu Val Thr Ser Thr Pro Ala Met Leu Leu Tyr Ala Ala Leu Phe
1               5                   10                  15

Ala Ala Ala Leu Leu Tyr Leu Ala Val Ala Val Arg Arg Gly Arg Gly
            20                  25                  30

Ala Gly Leu Pro Pro Gly Pro Thr Gly Leu Pro Leu Val Gly Ser Leu
        35                  40                  45

Leu Ser Leu Asp Pro Glu Leu His Thr Tyr Phe Ala Gly Leu Ala Ala
    50                  55                  60

Arg Tyr Gly Pro Ile Phe Ser Ile Arg Leu Gly Ser Lys Leu Gly Val
65                  70                  75                  80

Val Val Thr Ser Pro Ala Leu Ala Arg Glu Val Leu Arg Asp His Asp
                85                  90                  95

Leu Val Phe Ser Asn Arg Asp Thr Pro Asp Ala Ala Cys Ser Ile Ser
            100                 105                 110

Tyr Gly Gly Gly Gln Asn Ile Val Trp Asn Pro Val Gly Pro Thr Trp
        115                 120                 125

Arg Leu Leu Arg Arg Ile Cys Val His Glu Met Ile Gly Pro Ala Gly
    130                 135                 140

Leu Asp Ser Leu His Gly Leu Arg Arg Glu Phe Met Ala Thr Leu
145                 150                 155                 160

His His Leu Arg Ala Arg Ser Gly Glu Pro Val Asn Val Gly Ala Gln
                165                 170                 175

Met Phe Leu Thr Val Met Asn Val Thr Gly Ala Leu Trp Gly Gly
            180                 185                 190

Asn Val Gly Ser Glu Ser Glu Arg Thr Thr Val Gly Lys Glu Phe Arg
        195                 200                 205

Glu Leu Val Ala Asp Ile Thr Glu Leu Leu Gly Ala Pro Asn Val Ser
    210                 215                 220
```

Asp Phe Phe Pro Ala Leu Ala Pro Leu Asp Ile Gln Gly Ile Arg Asn
225                 230                 235                 240

Lys Ser Asp Leu Leu Lys Asp Arg Phe Asp Ile Phe Ala Arg Ile
            245                 250                 255

Ile Gln Lys Arg Thr Glu Ser Asp His Ala Ala Ala Gly Glu Thr
        260                 265                 270

Ala Ser Asp Phe Leu Glu Tyr Met Leu Lys Leu Glu Lys Glu Gly Gly
    275                 280                 285

Asp Gly Lys Thr Ala Phe Thr Met Thr Asn Val Lys Ala Leu Leu Met
290                 295                 300

Asp Met Val Ile Gly Thr Glu Thr Thr Ser Asn Thr Val Glu Trp
305                 310                 315                 320

Gly Met Ala Glu Met Leu Gln Asn Arg Gly Thr Leu Arg Lys Val Arg
                325                 330                 335

Glu Glu Leu Asp Ala Val Val Gly Arg Asp Gly Val Val Glu Glu Ser
            340                 345                 350

His Leu Pro Lys Leu His Tyr Leu Asn Leu Val Val Lys Glu Thr Leu
        355                 360                 365

Arg Leu His Pro Ala Leu Pro Leu Met Val Pro His Cys Pro Gly Glu
370                 375                 380

Asp Ala Thr Val Gly Gly His Arg Val Pro Ala Gly Ala Arg Val Phe
385                 390                 395                 400

Val Asn Val Trp Ala Ile Gln Arg Asp Pro Ala Val Trp Lys Asp Pro
                405                 410                 415

Glu His Phe Ile Pro Glu Arg Phe Leu Pro Ala Asp Gly Gly Gly Gly
            420                 425                 430

Arg Arg Leu Asp Phe Thr Gly Ser Gln Glu Tyr Met Pro Phe Gly
        435                 440                 445

Ser Gly Arg Arg Ile Cys Ala Gly Val Ala Met Ala Glu Arg Met Val
    450                 455                 460

Ala Tyr Ser Leu Ala Met Leu Val Gln Ala Phe Asp Trp Glu Leu Pro
465                 470                 475                 480

Ala Gly Glu Arg Leu Asp Leu Ala Glu Arg Phe Gly Ile Val Met Lys
                485                 490                 495

Lys Ala Thr Pro Leu Val Ala Val Pro Thr Pro Arg Leu Ser Asn Pro
            500                 505                 510

Gln Leu Tyr Ser Ala
        515

<210> SEQ ID NO 7
<211> LENGTH: 636
<212> TYPE: DNA
<213> ORGANISM: Oryza sativa

<400> SEQUENCE: 7
cccgtgtgct acctgtaccc atgggccgcg caatggcggc cgagttccgg cggcgcgggg     60
acgacccaga tgatgtgtat gggaccgtgg cacgcgtgct ctcctacatc cactacaccc    120
tccccagccc gccgtctcc gctaccacac gcctctgcgc acttacccg cacgacgtcg      180 tcgaccgcat cagcaccctc cctgacgagc tcctcagcaa ggtcgtctcc cacctccccg    240
tcaaggatgt cgcgcgcact accgctggag cccggtatgg tgctctatgc cgctcgcggc    300
ggatgagctc cccaccacgc cggactgccg ccgggtcccc tccgatccac cgcccactcc    360
gtcgcaggcc cgctccatgg cctgcatggc cggtcccgcc ttcctcactg acctccggac    420

```
cagttgacgg ttgcccaata gcctggtgct ctctgccgga accacctcat cacctcctcg    480
ggccatcttc atctacctcc tacgcccgt cccggtgcaa gcagaagcgg cggcaccgcg    540
gctgtggcat cggacgactt cgacatcaac cttgacagcc tcatgcgaga gctcgcccac    600
cgccgccccc actctgctcg gctggctcct ctctcc                              636
```

```
<210> SEQ ID NO 8
<211> LENGTH: 543
<212> TYPE: DNA
<213> ORGANISM: Oryza sativa

<400> SEQUENCE: 8
atggcggccg agttccggcg gcgcgggac gacccagatg atgtgtatgg accgtggca       60 cgcgtgctct cctacatcca ctacaccctc cccagcccgc cgtctccgc taccacacgc    120 ctctgcgcac ttaccccgca cgacgtcgtc gaccgcatca gcaccctccc tgacgagctc    180
ctcagcaagg tcgtctccca cctccccgtc aaggatgtcg cgcgcactac cgctggagcc    240
cggtatggtg ctctatgccg ctcgcggcgg atgagctccc caccacgccg gactgccgcc    300 gggtccctc cgatccaccg cccactccgt cgcaggcccg ctccatggcc tgcatggccg    360
gtcccgcctt cctcactgac ctccggacca gttgacggtt gcccaatagc ctggtgctct    420
ctgccggaac cacctcatca cctcctcggg ccatcttcat ctacctccta cgccctgtcc    480
cggtgcaagc agaagcggcg gcaccgcggc tgtggcatcg gacgacttcg acatcaacct    540
tga                                                                  543
```

```
<210> SEQ ID NO 9
<211> LENGTH: 180
<212> TYPE: PRT
<213> ORGANISM: Oryza sativa

<400> SEQUENCE: 9

Met Ala Ala Glu Phe Arg Arg Arg Gly Asp Asp Pro Asp Asp Val Tyr
1               5                   10                  15

Gly Thr Val Ala Arg Val Leu Ser Tyr Ile His Tyr Thr Leu Pro Ser
            20                  25                  30

Pro Pro Val Ser Ala Thr Thr Arg Leu Cys Ala Leu Thr Pro His Asp
        35                  40                  45

Val Val Asp Arg Ile Ser Thr Leu Pro Asp Glu Leu Leu Ser Lys Val
    50                  55                  60

Val Ser His Leu Pro Val Lys Asp Val Ala Arg Thr Thr Ala Gly Ala
65                  70                  75                  80

Arg Tyr Gly Ala Leu Cys Arg Ser Arg Arg Met Ser Ser Pro Arg
                85                  90                  95

Arg Thr Ala Ala Gly Ser Pro Ile His Arg Pro Leu Arg Arg Arg
            100                 105                 110

Pro Ala Pro Trp Pro Ala Trp Pro Val Pro Ser Ser Leu Thr Ser
        115                 120                 125

Gly Pro Val Asp Gly Cys Pro Ile Ala Trp Cys Ser Leu Pro Glu Pro
    130                 135                 140

Pro His His Leu Leu Gly Pro Ser Ser Ser Thr Ser Tyr Ala Leu Ser
145                 150                 155                 160

Arg Cys Lys Gln Lys Arg Arg His Arg Gly Cys Gly Ile Gly Arg Leu
                165                 170                 175

Arg His Gln Pro
```

<210> SEQ ID NO 10
<211> LENGTH: 559
<212> TYPE: DNA
<213> ORGANISM: Oryza sativa

<400> SEQUENCE: 10

```
ccgttcggac agtgaggaga aagccatgcc caccttcccc ttccccacgg cgcagatgaa    60
tgccgaagaa gagatggaat ctgagacagg aacgacagcg gttggagtgt gctggggcat   120
gagcggcgac aacctgccgc cggcgagcaa agtcaccgag atgctccgag agaacggctt   180
caccgtcgtc cgcctctaca cgccggacag cgccgctctc gtggcgctcg gcagcacagg   240
catctgcgtc gtcgtcggtg cgcccaacta cgacctcccc gccctggcgc acggcaggac   300
agccgccacg gccgcctgga tccgcgagaa catccaggcc tacccgacgg tgttattccg   360
gttcgtcgtc gtgggcaacg aggtctccag cgccgacatg cagctcctcg tcccggccat   420
ggagacgtcc acgccgcgct cgcggcggct ggtttgggac acatcaaggt gacgacgtcg   480
tccgcctgcg ccagcctgcc gccatgcagc tgctcccccg cgcagctgtt ccccgctgg    540 agcccgtgaa gaagagagg                                                559
```

<210> SEQ ID NO 11
<211> LENGTH: 447
<212> TYPE: DNA
<213> ORGANISM: Oryza sativa

<400> SEQUENCE: 11

```
atgcccacct tccccttccc cacggcgcag atgaatgccg aagaagagat ggaatctgag    60
acaggaacga cagcggttgg agtgtgctgg ggcatgagcg cgacaacct gccgccggcg   120 agcaaagtca ccgagatgct ccgagagaac ggcttcaccg tcgtccgcct ctacacgccg   180
gacagcgccg ctctcgtggc gctcggcagc acaggcatct gcgtcgtcgt cggtgcgccc   240
aactacgacc tccccgccct ggcgcacggc aggacagccg ccacggccgc ctggatccgc   300
gagaacatcc aggcctaccc gacggtgtta ttccggttcg tcgtcgtggg caacgaggtc   360
tccagcgccg acatgcagct cctcgtcccg gccatggaga cgtccacgcc gcgctcgcgg   420
cggctggttt gggacacatc aaggtga                                       447
```

<210> SEQ ID NO 12
<211> LENGTH: 148
<212> TYPE: PRT
<213> ORGANISM: Oryza sativa

<400> SEQUENCE: 12

```
Met Pro Thr Phe Pro Phe Pro Thr Ala Gln Met Asn Ala Glu Glu Glu
1               5                   10                  15

Met Glu Ser Glu Thr Gly Thr Thr Ala Val Gly Val Cys Trp Gly Met
            20                  25                  30

Ser Gly Asp Asn Leu Pro Pro Ala Ser Lys Val Thr Glu Met Leu Arg
        35                  40                  45

Glu Asn Gly Phe Thr Val Val Arg Leu Tyr Thr Pro Asp Ser Ala Ala
    50                  55                  60

Leu Val Ala Leu Gly Ser Thr Gly Ile Cys Val Val Gly Ala Pro
65                  70                  75                  80

Asn Tyr Asp Leu Pro Ala Leu Ala His Gly Arg Thr Ala Ala Thr Ala
                85                  90                  95
```

Ala Trp Ile Arg Glu Asn Ile Gln Ala Tyr Pro Thr Val Leu Phe Arg
            100                 105                 110

Phe Val Val Val Gly Asn Glu Val Ser Ser Ala Asp Met Gln Leu Leu
        115                 120                 125

Val Pro Ala Met Glu Thr Ser Thr Pro Arg Ser Arg Arg Leu Val Trp
    130                 135                 140

Asp Thr Ser Arg
145

<210> SEQ ID NO 13
<211> LENGTH: 559
<212> TYPE: DNA
<213> ORGANISM: Oryza sativa

<400> SEQUENCE: 13
ccgttcggac agtgaggaga aagccatgcc caccttcccc ttccccacgg cgcagatgaa       60
tgccgaagaa gagatggaat ctgagacagg aacgacagcg gttggagtgt gctgggcat      120 gagcggcgac aacctgccgc cggcgagcaa agtcaccgag atgctccgag agaacggctt      180
caccgtcgtc cgcctctaca cgccggacag cgccgctctc gtggcgctcg gcagcacagg      240
catctgcgtc gtcgtcggtg cgcccaacta cgacctcccc gccctggcgc acggcaggac      300
agccgccacg gccgcctgga tccgcgagaa catccaggcc tacccgacgg tgttattccg      360
gttcgtcgtc gtgggcaacg aggtctccag cgccgacatg cagctcctcg tcccggccat      420
ggagacgtcc acgccgcgct cgcggcggct ggtttgggac acatcaaggt gacgacgtcg      480
tccgcctgcg ccagcctgcc gccatgcagc tgctcccccg cgcagctgtt ccccgctgg      540 agcccgtgaa gaagagagg                                                   559

<210> SEQ ID NO 14
<211> LENGTH: 447
<212> TYPE: DNA
<213> ORGANISM: Oryza sativa

<400> SEQUENCE: 14
atgcccacct tccccttccc cacggcgcag atgaatgccg aagaagagat ggaatctgag       60
acaggaacga cagcggttgg agtgtgctgg ggcatgagcg gcgacaacct gccgccggcg      120
agcaaagtca ccgagatgct ccgagagaac ggcttcaccg tcgtccgcct ctacacgccg      180
gacagcgccg ctctcgtggc gctcggcagc acaggcatct gcgtcgtcgt cggtgcgccc      240
aactacgacc tccccgccct ggcgcacggc aggacagccg ccacggccgc ctggatccgc      300
gagaacatcc aggcctaccc gacggtgtta ttccggttcg tcgtcgtggg caacgaggtc      360
tccagcgccg acatgcagct cctcgtcccg gccatggaga cgtccacgcc gcgctcgcgg      420
cggctggttt gggacacatc aaggtga                                          447

<210> SEQ ID NO 15
<211> LENGTH: 78
<212> TYPE: PRT
<213> ORGANISM: Oryza sativa

<400> SEQUENCE: 15

Met Pro Trp Arg Pro Gly Arg Gly Glu Ser Ile Ala Tyr Pro Phe Ser
1               5                   10                  15

Val Gly Glu Trp Ala Pro Arg Glu His Ser Ser Pro Leu Pro Asn Thr
            20                  25                  30

Arg Ile Leu Ala Ile Ala Asn Leu Trp Leu Ser Pro Glu Thr Leu Ser
 35                  40                  45

Arg Asp Pro Ser Ala Gly Ile Ile Ala Ala Ile Cys Gly Tyr Leu Leu
 50                  55                  60

Asp Ile Cys Phe Leu Thr Gln Val Ala Gly Cys Tyr Cys Ser
 65                  70                  75

<210> SEQ ID NO 16
<211> LENGTH: 21
<212> TYPE: DNA
<213> ORGANISM: Artificial Sequence
<220> FEATURE:
<223> OTHER INFORMATION: Forward primer for cloning gDNA of OsDN-LTP8

<400> SEQUENCE: 16
cattggctaa tttgtaattg g                                         21

<210> SEQ ID NO 17
<211> LENGTH: 25
<212> TYPE: DNA
<213> ORGANISM: Artificial Sequence
<220> FEATURE:
<223> OTHER INFORMATION: Reverse primer for cloning gDNA of OsDN-LTP8

<400> SEQUENCE: 17
ctatggtgaa caatagaaaa ctgtg                                     25

<210> SEQ ID NO 18
<211> LENGTH: 26
<212> TYPE: DNA
<213> ORGANISM: Artificial Sequence
<220> FEATURE:
<223> OTHER INFORMATION: Forward primer for cloning gDNA of OsCYP76M5

<400> SEQUENCE: 18
gattagctcc attttccacc taagag                                    26

<210> SEQ ID NO 19
<211> LENGTH: 28
<212> TYPE: DNA
<213> ORGANISM: Artificial Sequence
<220> FEATURE:
<223> OTHER INFORMATION: Reverse primer for cloning gDNA of OsCYP76M5

<400> SEQUENCE: 19
ctacaattat agcccgagat ttaaaacc                                  28

<210> SEQ ID NO 20
<211> LENGTH: 32
<212> TYPE: DNA
<213> ORGANISM: Artificial Sequence
<220> FEATURE:
<223> OTHER INFORMATION: Forward primer for cloning gDNA of OsFBX25

<400> SEQUENCE: 20
ctgctgaggc ccgtgtgcta cctgtaccca tg                             32

<210> SEQ ID NO 21
<211> LENGTH: 30
<212> TYPE: DNA
<213> ORGANISM: Artificial Sequence
<220> FEATURE:
<223> OTHER INFORMATION: Reverse primer for cloning gDNA of OsFBX25

<400> SEQUENCE: 21

<210> SEQ ID NO 22
<211> LENGTH: 33
<212> TYPE: DNA
<213> ORGANISM: Artificial Sequence
<220> FEATURE:
<223> OTHER INFORMATION: Forward primer for cloning gDNA of OsGH17

<400> SEQUENCE: 22
ctgctgaggc cgttcggaca gtgaggagaa agc        33

<210> SEQ ID NO 23
<211> LENGTH: 33
<212> TYPE: DNA
<213> ORGANISM: Artificial Sequence
<220> FEATURE:
<223> OTHER INFORMATION: Reverse primer for cloning gDNA of OsGH17

<400> SEQUENCE: 23
ccgctgaggc ctctcttctt cacgggctcc agc        33

<210> SEQ ID NO 24
<211> LENGTH: 31
<212> TYPE: DNA
<213> ORGANISM: Artificial Sequence
<220> FEATURE:
<223> OTHER INFORMATION: Forward primer for cloning cDNA of OsDN-LTP9

<400> SEQUENCE: 24
ctgctgaggg gtctctcttg cactcgtgag c          31

<210> SEQ ID NO 25
<211> LENGTH: 34
<212> TYPE: DNA
<213> ORGANISM: Artificial Sequence
<220> FEATURE:
<223> OTHER INFORMATION: Reverse primer for cloning cDNA of OsDN-LTP9

<400> SEQUENCE: 25
ccgctgaggc aaaatcaaga acagtagcag ccag       34

<210> SEQ ID NO 26
<211> LENGTH: 19
<212> TYPE: DNA
<213> ORGANISM: Artificial Sequence
<220> FEATURE:
<223> OTHER INFORMATION: Forward primer for real-time RT-PCR analysis of
      OsDN-LTP8 gene

<400> SEQUENCE: 26
accagtgaag agaaaggcg                        19

<210> SEQ ID NO 27
<211> LENGTH: 20
<212> TYPE: DNA
<213> ORGANISM: Artificial Sequence
<220> FEATURE:
<223> OTHER INFORMATION: Reverse primer for real-time RT-PCR analysis of
      OsDN-LTP8 gene

<400> SEQUENCE: 27
cttgacattt gcgaactggc                       20

<210> SEQ ID NO 28
<211> LENGTH: 20

```
<212> TYPE: DNA
<213> ORGANISM: Artificial Sequence
<220> FEATURE:
<223> OTHER INFORMATION: Forward primer for real-time RT-PCR analysis of
      OsFBX25 gene

<400> SEQUENCE: 28
agttgacggt tgcccaatag                                                   20

<210> SEQ ID NO 29
<211> LENGTH: 20
<212> TYPE: DNA
<213> ORGANISM: Artificial Sequence
<220> FEATURE:
<223> OTHER INFORMATION: Reverse primer for real-time RT-PCR analysis of
      OsFBX25 gene

<400> SEQUENCE: 29
gtagatgaag atggcccgag                                                   20

<210> SEQ ID NO 30
<211> LENGTH: 22
<212> TYPE: DNA
<213> ORGANISM: Artificial Sequence
<220> FEATURE:
<223> OTHER INFORMATION: Forward primer for real-time RT-PCR analysis of
      OsGH17 gene

<400> SEQUENCE: 30
gaatctgaga caggaacgac ag                                                22

<210> SEQ ID NO 31
<211> LENGTH: 19
<212> TYPE: DNA
<213> ORGANISM: Artificial Sequence
<220> FEATURE:
<223> OTHER INFORMATION: Reverse primer for real-time RT-PCR analysis of
      OsGH17 gene

<400> SEQUENCE: 31
atctcggtga ctttgctcg                                                    19

<210> SEQ ID NO 32
<211> LENGTH: 21
<212> TYPE: DNA
<213> ORGANISM: Artificial Sequence
<220> FEATURE:
<223> OTHER INFORMATION: Forward primer for real-time RT-PCR analysis of
      OsDN-LTP9 gene

<400> SEQUENCE: 32
ttcatctcca cttcccaaca c                                                 21

<210> SEQ ID NO 33
<211> LENGTH: 21
<212> TYPE: DNA
<213> ORGANISM: Artificial Sequence
<220> FEATURE:
<223> OTHER INFORMATION: Reverse primer for real-time RT-PCR analysis of
      OsDN-LTP9 gene

<400> SEQUENCE: 33
cagcaacctg tgtcaagaaa c                                                 21
```